US006171864B1

(12) United States Patent
Coughlan et al.

(10) Patent No.: US 6,171,864 B1
(45) Date of Patent: *Jan. 9, 2001

(54) CALRETICULIN GENES AND PROMOTER REGIONS AND USES THEREOF

(75) Inventors: Sean J. Coughlan, Des Moines; Ron J. Winfrey, Jr., Johnston, both of IA (US)

(73) Assignee: Pioneer Hi-Bred International, Inc., Johnston, IA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/675,816

(22) Filed: Jul. 5, 1996

(51) Int. Cl.$^7$ ............... C12N 1/21; C12N 5/04; C12N 15/29; C12N 15/84
(52) U.S. Cl. ............ 435/469; 435/410; 435/415; 435/416; 435/419; 435/426; 435/428; 435/69.1; 435/252.3; 800/278; 800/287; 536/23.6; 536/24.1
(58) Field of Search .................. 435/69.1, 70.1, 435/172.1, 252.3, 254.11, 325, 419, 410, 415, 418, 116, 428, 430, 469, 424, 426; 514/12; 536/23.6, 24.1; 800/278, 287

(56) References Cited

U.S. PATENT DOCUMENTS

| 5,097,025 | * | 3/1992 | Benfey et al. | 536/27 |
| 5,426,097 | * | 6/1995 | Stern et al. | 514/12 |
| 5,591,716 | * | 1/1997 | Siebert et al. | 514/12 |

OTHER PUBLICATIONS

Sambrook et al. Molecular Cloning: A Laboratory Manual, Second Edition, Cold Spring Harbor Press, Cold Spring Harbor, pp. 9.49–9.51, 1989.*
George et al. Macromolecular Sequencing and Synthesis: Selected Methods and Applications, ed. DH Schlesinger, Alan R. Liss, Inc., NY, pp. 127–149, 1988.*
Chen et al. Identification and characterization of cDNA clones encoding plant calreticulin in barley. The Plant Cell. vol. 6, pp. 835–843, Jun. 1994.*
Denecke et al. The tobacco homolog of mammalian calreticulin is present in protein complexes in vivo. The Plant Cell. vol. 7, pp. 391–406, Apr. 1995.*
Napier et al. Calcium–binding protein—maize. EMBL Accession No. S49818, Mar. 5, 1995.*
Kwiatkowski et al., "Cloning of two cDNAs encoding calnexin–like and calreticulin–like proteins from maize (*Zea mays*) leaves: identification of potential calcium–binding domains,"*Gene* 165: 219–222, 1995.
"*Arabidopsis thaliana* Columbia calnexin homolog gene, complete eds," GenBank Database Accession No. U08315, Apr. 22, 1994.
"*Arabidopsis thaliana* calnexin homolgo," GenBank Database Accession No. Z18242, May 11, 1995.
"H. tuberosus mRNA for calnexin," GenBank Database Accession No. Z35108, Jul. 11, 1994.
"Glycine max calnexin nRNA, complete eds," GenBank Database Accession No. U20502, Nov. 8, 1995.
"*Z. mays* CNX mRNA," GenBank Database Accession No. X77569, Jan. 10, 1996.
"*Z. mays* CRH and mRNA," GenBank Database Accession No. X78057, Jan. 10, 1996.
"Hordeum vulgare calreticulin (CRH1) mRNA, partial cds," GenBank Database Accession No. L27348, Jul. 27, 1994.
"Hordeum vulgare calreticulin (CRH2) mRNA, partial cds," GenBank Database Accession No. L27349, Jul. 27, 1994.
"*Z. mays* mRNA for calreticulin precursor," GenBank Database Accession No. X89813, Jul. 26, 19995.
"*Zea mays* CRT1 gene for calcium–binding protein," GenBank Database Accession No. Z46772, Nov. 23, 1994.
"N. tabacum mRNA for calreticulin," GenBank Database Accession No. X85382, Sep. 12, 1995.
"*P. argentatum* mRNA for calreticulin," GenBank Database Accession No. X82578, Nov. 11, 1994.
"*Arabidopsis thaliana* calreticulin (AtCRTL) mRNA, partial cds," GenBank Database Accession No. U27698.
"C. annuum PCRTC mRNA," GenBank Database Accession No. X80756 Sep. 8, 1995.
"*A. thaliana* transcribed sequence; clone FAFE28–1; 5'end; similar to calreticulin precursor—Caenorhabditis elegans, "GenBank Database Accession No. Z26445, Sep. 24, 1993.

* cited by examiner

Primary Examiner—Elizabeth Kemmerer
(74) Attorney, Agent, or Firm—Seed IP Law Group PLLC

(57) ABSTRACT

Isolated nucleic acid molecules are provided which encode calreticulin and calnexin. Also provided are vectors which are capable of expressing such nucleic acid molecules, host cells which contain such vectors, and polypeptides encoded by the afore-mentioned nucleic acids. In addition, nucleic acid molecules are provided which comprise calreticulin or calnexin promoters.

19 Claims, 21 Drawing Sheets

```
   1  CTAGAAATGG CGAACCCTAA ATCTCTCTCA CTCTTTCTTC TCTCGCTTTT AGCGATCGCT
  61  TCTGCAGAAG TCTTCTTCGA GGAGCGTTTC GAAGATGGAT GGGAAAATAG GTGGGTTAAA
 121  TCTGATTGGA AGAAAGATGA AATACAGCT GGTGAATGGA ATTATACCTC TGGAAAGTGG
 181  AATGGAGACC CTAATGACAA AGGTATTCAA ACAAGTGAAG ATTATAGGTT CTATGCTATT
 241  TCAGCTGAAT TCCCTGAATT CAGTAATAAA GATAAGACTC TAGTCTTCCA ATTTTCTGTC
 301  AAGCATGAAC AGAAGCTTGA CTGTGGTGGT GGTTACATGA AGTTGCTCAG TAGTAGCACT
 361  GACCAGAAGA AATTTGGTGG TGACACTCCA TACAGTATCA TGTTTGGACC CGATATATGT
 421  GGCTACAGCA CCAAAAAAGT TCATGCTATC CTTAACTACA ATGATACAAA CCACTTGATC
 481  AAAAAGGAAG TTCCATGTGA AACCGACCAG TTAACTCATG TTTACACATT GGTCATCCGT
 541  CCAGATGCTA CTTATAGCAT TCTTATCGAC AATGTGGAGA AGCAAACTGG TAGTTTGTAC
 601  ACTGACTGGG ATCTTCTTCC ACCTAAGAAA ATTAAGGACC CTGAGGCCAA GAAACCAGAA
 661  GATTGGGATG AGAAGGAGTA TATTCCTGAC CCTGAGGATA AGAAACCAGA GGGTTATGAT
 721  GACATTCCAA AGGAGATTCC AGATCCCGAT GCCAAGAAGC CTGAGGATTG GGATGATGAG
 781  GAAGATGGTG AATGGACTGC CCCAACCATT GCCAACCCTG AGTACAAGGG TCCATGGAAA
 841  CCCAAGAAAA TTAAGAACCC CAACTACAAG GGCAAGTGGA AAGCACCAAT GATCGACAAC
 901  CCAGATTTCA AGGATGACCC AGAAATCTAT GTTTACCCCA ACTTGAAGTA TGTTGGTATT
 961  GAATTGTGGC AGGTGAAATC TGGAACCTTG TTTGACAATG TCTTGATTTG CAATGACCCT
1021  GAGTATGCTA AGCAGCTGGC TGAAGAGACA TGGGGAAAGA ACAAAGATGC TGAGAAGGCA
1081  GCATTTGAAG AGGCAGAGAA GAAGAAAGAA GAGGAGGAAT CAAAGGATGA TCCAGCTGAT
1141  TCTGATGCTG ACGAGGACGA TGATGATGCT GATGACACTG AAGGAGAAGA TGATGGTGAA
1201  AGCAAATCAG TGCAGCAGAA GACAGTGCTG AGGACGTACA TGATGAACTG TAGAGAGGAA
1261  GCACTTTTGC TGACAAGCGA TGGAGATGAG CGGGGGCATA TAGTAGTACT CCCAAAATTT
1321  TTCTATTTTC TTTTGATTCG TAGCTGTAGG AGCTCTTGTA GGGAAAGAAA AATAGAGAAA
1381  GTTGCACTGC AGAACTGCTT GGCTGATTGT TTTAGTCCCC ATTTAAAACC TGTCTGAGCC
1441  TTTAGAACAA AGAAGATGTC CTTTTATAAT CAAATTTATG ATTTGAATGT TCTACAAAAA
1501  AAAAAAAAAA AAA
```

*Fig. 1A*

```
   1  MANPKSLSLF LLSLLAIASA EVFFEERFED GWENRWVKSD WKKDENTAGE WNYTSGKWNG
  61  DPNDKGIQTS EDYRFYAISA EFPEFSNKDK TLVFQFSVKH EQKLDCGGGY MKLLSSSTDQ
 121  KKFGGDTPYS IMFGPDICGY STKKVHAILN YNDTNHLIKK EVPCETDQLT HVYTLVIRPD
 181  ATYSILIDNV EKQTGSLYTD WDLLPPKKIK DPEAKKPEDW DEKEYIPDPE DKKPEGYDDI
 241  PKEIPDPDAK KPEDWDDEED GEWTAPTIAN PEYKGPWKPK KIKNPNYKGK WKAPMIDNPD
 301  FKDDPEIYVY PNLKYVGIEL WQVKSGTLFD NVLICNDPEY AKQLAEETWG KNKDAEKAAF
 361  EEAEKKKEEE ESKDDPADSD ADEDDDDADD TEGEDDGESK SDAAEDSAED VHDEL*
```

*Fig. 1B*

TISSUE SPECIFIC EXPRESSION AND GENE
COPY NUMBER OF THE CASTOR CALRETICULIN GENE.

```
 -59 ACCGGTAATACCGAAGAAGAAGATCTGCTATAAATAACGCTCTCACTCTCTTACTCTACAGCTCCAAAATTCTCT    16
  17 CT
        CTAGAAATGGCGAACCCTAAATCTCTCTCACTCTTTCTTCTCTCGCTTTTAGCGATCGCTTCTGCAGAAGTCT    91
            MetAlaAsnProLysSerLeuSerLeuPheLeuLeuSerLeuLeuAlaIleAlaSerAlaGluVal           22

GTATCTATCCATCTTACTTTAACACTGTCCATACGTCGTCTTTATGATTACTTT   166
  92 TCTTCGAGGAGCGTTTCGAAG
       PhePheGluGluArgPheGluAsp>                                                      30

167 CTTCTTGTGTTTTTATTCCGTGGATCTATTTGCTTTTAACTGTTTCTTTGCTTATCGCGTAATTAAGGATAGAAC   241
 242 TGTAATTAGTTTTGATAGATCTGTTAATAATGTTTGGTTTTGCTTTCGGCAATGATGATTGATCAGAAATTAGAA   316
 317 ATGGAACTCCTGGTTTGTGTTTGCTTGTTGAGAAAAGAATGCGATCAGGTGTTAATGTACTGGATTGATCGAGCA   391
 392 TTTGTTAGATCTGTTTGGATAATGTGTTTTTGTGATAATTCGTGAGAAATGGTCGTGTTTGATTATATGAAATT   466
 467 TAAATTTTGGAAAATTAGTAATTACACGTGCATATTTTCATTAGCCGGAATTGGTCAAAGTTTGACTCTCTATTT   541
 542 GTTTTCAGCGTTAGCCTTTTCTAACTAAAAAGCACATTTGATTGTACCTTTCTTGAAATTTTACCGTTTATATTT   616
 617 CAGTTTGCATAACTTTGCTTAGTGAAACTGAACAGTAAAATTAAGTATGCATAATCCAACAATTGCTAATTACAT   691
 692 TTCTGTTTTACTGGTTTGCAG
                         ATGGATGGGAAAATAGGTGGGTTAAATCTGATTGGAAGAAAGATGAGAATACAG   766
                          GlyTrpGluAsnArgTrpValLyaSerAspTrpLysLyaAspGluAsnThr        47

GTATGATTGTTTGCTCAACAA   841
 767 CTGGTGAATGGAATTATACCTCTGGAAAGTGGAATGGAGACCCTAATGACAAAG
       AlaGlyGluTrpAsnTyrThrSerGlyLysTrpAsnGlyAspProAsnAspLysGly>                     66
                                                         *
 842 ATACTAACTATTTGAGAGTTTCCAAATAAAATTTCTTTTAGCTGTTGTACGATTTTAATGATTTTAACATCTTGA   916
 917 TGCAG
        GTATTCAAACAAGTGAAGATTATAGGTTCTATGCTATTTCAGCTGAATTCCCTGAATTCAGTAATAAAGA    991
          IleGlnThrSerGluAspTyrArgPheTyrAlaIleSerAlaGluPheProGluPheSerAsnLysAsp        89

992 TAAGACTCTAGTCTTC CAATTTTCTGTCAAGCATGAACAGAAGCTTGACTGTGGTGGTGGTTACATGAAGTTGCT  1066
       LysThrLeuValPhe(GlnPheSerValLysHisGluGlnLysLeuAspCysGlyGlyGlyTyrMetLysLeuLeu)  114

GTGAGGACAGTTTACGGTTTTAATTTT  1141
1067 CAGTAGTAGCACTGACCAGAAGAAATTTGGTGGTGACACTCCATACAG
       SerSerSerThrAspGlnLysLysPheGlyGlyAspThrProTyrSer>

1142 GTGTTTTTTCTTTTTAGTTCTTCTAATGAAATACTAACTGGTTATCTTTTTTGGTTGACTTCAG
                                                                  TATCATGTTTG  1216
                                                                  (IleMetPhe     133

1217 GACCCGATATATGTGGC TACAGCACCAAAAAAGTTCATGCTATCCTTAACTACAATGATACAAACCACTTGATCA  1291
       GlyProAspILeCysGly)TyrSerThrLysLysValHisAlaIleLeuAsnTyrAsnAspThrAsnHisLeuIle  158
                                                                      *
1292 AAAAGGAAGTTCCATGTGAAACCGACCAGTTAACTCATGTTTACACATTGGTCATCCGTCCAGATGCTACTTATA  1366
       LysLysGluValProCysGluThrAspGlnLeuThrHisValTyrThrLeuValIleArgProAspAlaThrTyr   183

1367 GCATTCTTATCGACAATGTGGAGAAGCAAACTGGTAGTTTGTACACTGACTGGGATCTTCTTCCACCTAAGAAAA  1441
       SerIleLeuIleAspAsnValGluLysGlnThrGlySerLeuTyrThrAspTrpAspLeuLeuProProLysLys   208
```

*Fig. 3A*

```
                              GTAATCACTTTGCACTTTAATTCTTCTAACATTGTACTGGCATTTGAGTTTT  1516
1442  TTAAGGACCCTGAGGCCAAGAAA
      (IleLysAspProGluAlaLysLys                                                         216

1517  GGTGGTTACTCAACTTTTAAACTTGATGGCAG
                                      CCAGAAGATTGGGAT GAGAAGGAGTATATTCCTGACCCTGAGG  1591
                                      ProGluAspTrpAsp)GluLysGluTyrIleProAspProGlu    230

GTAATGACATGTCAAATCACCTAGTCTGCCTGGTTCACGCCATATTTTCTAGTGACAACAA  1666
1592  ATAAGAAACCAGAG
      AspLysLysProGlu                                                                   235

1667  AAATGTATATCTGAAGCTAATGTTTTTCTTCTGTTTCTTTTAG
                                                  GGTTATGATGACATTCCAAAGGAG ATTCCAGA  1741
                                                  GlyTyrAspAspIleProLysGlu(IleProAsp  246

GTAGATATATTGAAATTCTTGTGTTTGTTTCTACTGCACCTTTATTTGGTAGAAAAGTA  1816
1742  TCCCGATGCCAAGAAG
      ProAspAlaLysLys                                                                   251

1817  GATTCTGATGAAGGTGGCTTACAATTGTAG
                                    CCTGAGGATTGGGAT GATGAGGAAGATGGTGAATGGACTGCCCCA  1891
                                    ProGluAspTrpAsp)AspGluGluAspGlyGluTrpThrAlaPro    266

GTCTGTGGTTTATGATCAAGTTGCAGCCTCTGC  1966
1892  ACCATTGCCAACCCTGAGTACAAGGGTCCATGGAAACCCAAG
      ThrIleAlaAsnProGluTyrLysGlyProTrpLysProLys                                        280

1967  TATCCAATGTGTAATTTGGAGCCATAACTTATGCGATTTTGTTCTTTTTGCAG
                                                          AAAATTAAGAACCCCAACTACA  2041
                                                          LysIleLysAsnProAsnTyr    287

2042  AGGGCAAGTGGAAAGCACCAATGATCGACAACCCAGATTTCAAGGATGACCCAGAAATCTATGTTTACCCCAACT  2116
      LysGlyLysTtpLysAlaProMetIleAspAsnProAspPheLysAspAspProGluIleTyrValTyrProAsn    312

GTAATTTTCTTTCCATATTTTATCTAGTTGTTTGAATTTGCCCGGT  2191
2117  TGAAGTATGTTGGTATTGAATTGTGGCAG
      LeuLysTyrValGlyIleGluLeuTrpGln                                                    322

2192  GACTAACAAAACAAATCCCACTATTGTGTCAG
                                      GTGAAATCTGGAACCTTGTTTGACAATGTCTTGATTTGCAATG  2266
                                      ValLysSerGlyThrLeuPheAspAsnValLeuIleCysAsn    336

GTATGTGGCCTTTGCATATTTA  2341
2267  ACCCTGAGTATGCTAAGCAGCTGGCTGAAGAGACATGGGGAAAGAACAAAGAT
      AspProGluTyrAlaLysGlnLeuAlaGluGluThrTrpGlyLysAsnLysAsp                             354

2342  AATTATAATCTTCAAAAAAGACTCTTGTCTCGATACTTTACTGAGATTGTCAAATTTCAG
                                                                  GCTGAGAAGGCAGCA  2416
                                                                  AlaGluLysAlaAla    359
```

*Fig. 3B*

```
                                    GTACTTCCTTTCTCATAAATTGCAGTTTGAATTTGAATGGCT  2491
2417  TTTGAAGAGGCAGAGAAGAAGAAAGAAGAGGAG
      PheGluGluAlaGluLysLysLysGluGluGlu                                            370

2492  TTTCTTGGATGGAATTAGCTAGAGAGGTTCTGATGCTGCAAATAGCTAACTCATAGGTTTAAATTTTTTCAG
                                                                              GAA  2566
                                                                              Glu   371

GTAAGCCTGCGAACTGTTTCCTGAAACAAATTTAGTTTGTTTCTGTGA  2641
2567  TCAAAGGATGATCCAGCTGATTCTGAT
      SerLysAspAspProAlaAspSerAsp                                                  380

2642  CTTTTACCTAATTGAACCATTTTTTTCAG
                              GCTGACGAGGACGATGATGATGCTGATGACACTGAAGGAGAAGATG  2716
                              AlaAspGluAspAspAspAspAlaAspAspThrGluGlyGluAsp   395

GTAAATTCTCTAACTTTTATGATTG  2791
2717  ATGGTGAAAGCAAATCAGATGCAGCAGAAGACAGTGCTGAGGACGTACAT
      AspGlyGluSerLysSerAspAlaAlaGluAspSerAlaGluAspValHis                          412

2792  TGGTAACTGGTAAAGAAGCATTTAATTTGTGTGCACTGATAAAATTTGTCAATTGTGTTGTGTTGGCAG
                                                                      GATGAA  2866
                                                                      AspGlu   414

2867  CTGTAGAGAGGAAGCACTTTTGCTGACAAGCGATGGAGATGAGCGGGGGCATATAGTAGTACTCCCAAAATTTTT  2941
      Leu***

2942  CTATTTTCTTTTGATTCGTAGCTGTAGGAGCTCTTGTAGGGAAAGAAAAATAGAGAAAGTTGCACTGCAGAACTG  3016
3017  CTTGGCTGATTGTTTTAGTCCCCATTTAAAACCTGTCTGAGCCTTTAGAACAAAGAAGATGTCCTTTTATAATCA  3091
3092  AATTTATGATTTGAATGTTCTACAAAAAAAAAAAAAAAAA                                     3132
```

*Fig. 3C*

```
-1844  GCATGCTAAATCACTAGGTCCTAAAGGTTCAGACCCTCACAAAGCTGCTGTCATTGGCGACACAATCGGCGACCC  -1770
            Sph I
-1769  TCTTAAGGACACTTCGGGTCCATCACTTAATATCCTGATCAAGCTCATGGCAGTCGAGTCATTGGTGTTTGCTCC  -1695
-1694  ATTCTTTGCTGCTCACGGAGGTCTGCTGTTCAAATTGCTGTAATTTAAGCAAGCAAGTTATAACCCGAGCAAAGA  -1620
-1619  TATGTTGTTACGACGGAAGCAATATCATGTAATTGAGTTCTCACTGTTATAGTTTCAACATGTAAAAAGAATATA  -1545
-1544  AAAAAAGAAACAGATATATGGCTTTGCTGCTTCTACATTGCTAAATTTACCGTGAATAAAATTGTAGTTTCATAT  -1470
-1469  ATACATTTCTTCCTTTTGCAGTCTAGCATTGGCCTTAATAACACCGATTCACAACTGGAACTGAACTAGCCGTTT  -1395
-1394  TGGAGGCTTGGCTTGTCTTACTAAGGGGTTCCCACATGACACCCATTAGAGACTGAACGTAAACCTTAGATTAAT  -1320
-1319  GGCAATTTGCAAGATATGTAAATGCAATGACACACCCAAAATCATATAGACGAGGTTAACTAATGTTTCAAATTC  -1245
-1244  GAACTTTGAAATGCATTTACATTATAATTTTTGAAAAAGTATTTTATCATCTCCAAGTATCATATTCAGTAAGTT  -1170
-1169  CTAGGGTACTGCTTTCTCCATATATATATTCCATACTCGGGTAAATTGTAGATTAACTATATATATATATATTTT  -1095
-1094  GTAAAGACAGTGGCTGACCCGTCACCCTATGCTCTAACCTTAATGATTCGCTTCAAACGCAAGCATCCAAATCAG  -1020
-1019  CCAATAAAAGTAAGTGCCGGCCCCCACTTTTCTGACAGAAATTATTATGCAAGTGTACAACAACAAGGCCTACTG  -945
 -944  AAAATCATCACTTGTGGTGGACTTTAGTACCTTGTTTAAGCATACTCATTTGTTATTATACCCATAACAAGAACC  -870
 -869  CTATCCCTAATTGCATAGATTCTTATTTATTTAAGGGAATGAAATGTCATGAACTGAATTCTTAATTATTTCCTT  -785
                                                                  Eco RI
 -794  TTTTCTTTTTGCTTAACATATTTGAATTATACCACAAAGGGTAATTTTTAATTTTTTAGATAGTTAGATTATCTT  -720
 -719  TAAAGGTTGTATTATAAAAATAATAAATTTCCATTAATATCAACTGGTGGTATATAAGAAAACACTTTGAAATTC  -645
 -644  TTGTAATTTTCACAGATATTTAGTTTTTTTTTTTAAAAAATTTGTTTTAGATAAAACATAATTAATCTTACTTT  -570
 -569  TTCAAAAATAATCTATTAGAAAATTTTTAAATCTGTTTCTTCCTTTTTAATACTCAACCAATAATTTTAAACATT  -495
 -494  AACGCCACTAGTGTATTGCTTTTTACCTTAATAGATGATTCTAGAGAATTAATTTCTAATTCTTAATTAAACATA  -420
                                          Xba I         Pu box
 -419  TAGCCAAATCCGGAACCCTATTAAAACCCTTCTAATTTTATTATTATCTATATGAGGAAATCACAAGCAACCTTT  -345
                  CTF/CBP-hs                                G box
 -344  TCATCAGGCTGGGTCCACAATTACCAATCACCCCTCATAGCACGCCACGTGTCACTCAATTTTCAGTAACAGAAT  -270
            CAAT box                          G box
 -269  AAACACATAAAAGGCCATTCTTAATCCAAATACGATATTACCACGTGTAAAATACTACTTGCCCTCTACAATTCG  -195
            CTF/CBP-hs                                              AP1
 -194  TGGAATCTCCCAATCGTATTATGCCATGTCATACTAATGACACTTCAATCCGAGTTGCCGATATACTATTAGTCC  -120
 -119  ACGTAACTGGATGTTGTCCAGCTAGGATGTTTACCCATAGTAAAATACATATTTTAACTAACCGGTAATACCGAA  -45
                                                                       Age I
  -44  GAAGAAGATCTGCTATAAATAACGCTCTCACTCTCTTACTCTACAGCTCCAAAATTCTCTCTCTAGAAAATG      27
           BglII TATA box              ST            Xba I
```

*Fig. 5*

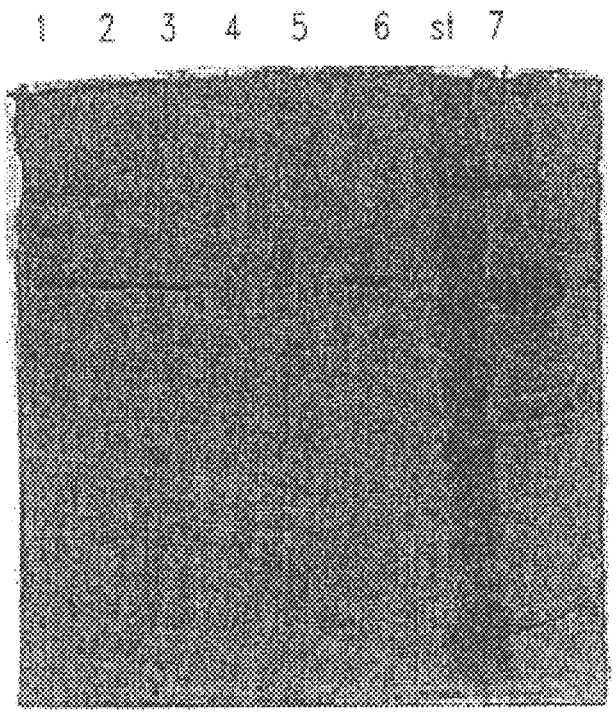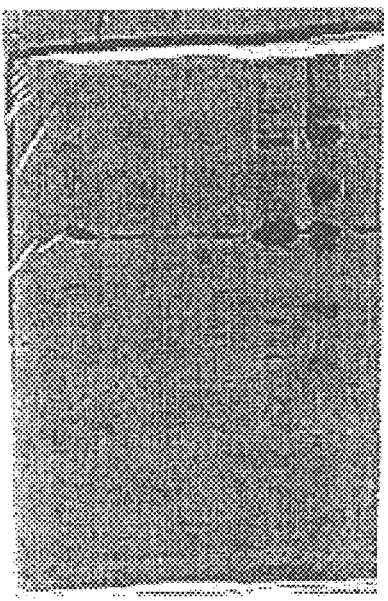
Fig. 9B

```
.........................................GCATGCT   -751
GGCAAGAGTTCAACTCCTGCCAACTTTATTCTCCTTGAAATTAATCAGGT  -701
AAACCATAATAGTGATTCTGTGAAATTAAAGTGTGGTTGGGGTTAAGAAC  -651
TAAGCATTCCACTAACTAGAAACAATCGCAGGTTAACAAGCACCACAACG  -601
ATCGTTGGAAGAAAATTCACTCCCCGAGCTAGCTAGCCAAATTTGCGAGA  -551
AGCTCGACTGCTTCATCTCCCTTGCAGATGATGTTCATATGTGGAATTCA  -501
CCTCCCACCACTGCCACTGCCAAAACATCCAGCGCAAGTACCCGAGTCGC  -451
CACACTTGAGCCACTTTTACATTATATAGATAAATGTATATTGCACCATC  -401
CATGGCATGAAAGCTAGATGAAGTGCATCCGATATGAGGCTTGAGAACAG  -351
AACCATGAGATAGATTCGCAAATCTCAACCATTGCATGTACTGTTGGCAC  -301
AGTGGAGTTTGCTTATGTCCTTGAAACACCAAGGAAGCTAATCATTTTGA  -251
TTAATTTTCATTTCGCGTTATTCTATATTCTCTTTTAATTAGTTCTTAAG  -201
CAACCACTATTATGATACAATGTACATGTCTAATCTGATTTATTTATGCA  -151
ATCAAAAAATTTATTCGGAAAATTCTTGTATACACCAAACCAAATATATA  -101
TATACGTATGTATAAATATTTATAATACTTGATTTTTTTTAAAATATAAT   -51
TTTTTTATGAAATTAAAATTTAAATAATTACTTACAGTTCTAATTAAAAT    -1
ACTTTATTTTATATTACAATTTTATTATTTATAAATTCAATAAGTTAATC    50
CCTTAGTAGTTAATAATTTTTTTATTCTACCATATATATTACTCATAAAA   100
GATTTCGACTATATAGAGATATGGAATTTGAAGTCTTTTCTCATTAGTGG   150
GCGATCCGATAGTGCACCAATAAACGAATATCAGACCCAAAAACCATGGG   200
CTTGGCCAATAAAACGAAAGCAACATAACAGTTGAGACTTGGGACCGGGT   250
CAAGCCCGCAAGTGTAAAAACAAATATTCCACCGAAGTAACATATGAGAA   300
TTGCTGGAGTTGCTTACTTGTCGAACTCCGATTGGTTGGATTCACGTGGC   350
ACGTAAATTGATTGGCGGAAACAACACGAAGGCAGTGATTTCCAAGATCT   400
TTAAGTATACACGCATCGCAAAATGTAGCAAAACCAAATCTGTTAATCTA   450
GAAGTTGTTTTTCCTTTTCTTTCCTTTCCTTTCCTTTCCTTGCCTTGTGT   500
TAGATTAGATTTTAGATTCAGATCAGATCAATAATTATACTTAGCTAAAC   550
CTAGGAGGAGTAGCTAGGGTTTTGAGAGTTTTTGGGATACCAAGAGATG    599
```

*Fig. 12*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1514 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 7..1254

(xi) SEQUENCE DESCRIPTION: SEQ ID NO:1:

```
CTAGAA ATG GCG AAC CCT AAA TCT CTC TCA CTC TTT CTT CTC TCG CTT        48
       Met Ala Asn Pro Lys Ser Leu Ser Leu Phe Leu Leu Ser Leu
        1               5                  10

TTA GCG ATC GCT TCT GCA GAA GTC TTC TTC GAG GAG CGT TTC GAA GAT        96
Leu Ala Ile Ala Ser Ala Glu Val Phe Phe Glu Glu Arg Phe Glu Asp
 15              20                  25                  30

GGA TGG GAA AAT AGG TGG GTT AAA TCT GAT TGG AAG AAA GAT GAG AAT       144
Gly Trp Glu Asn Arg Trp Val Lys Ser Asp Trp Lys Lys Asp Glu Asn
                 35                  40                  45

ACA GCT GGT GAA TGG AAT TAT ACC TCT GGA AAG TGG AAT GGA GAC CCT       192
Thr Ala Gly Glu Trp Asn Tyr Thr Ser Gly Lys Trp Asn Gly Asp Pro
                     50                  55                  60

AAT GAC AAA GGT ATT CAA ACA AGT GAA GAT TAT AGG TTC TAT GCT ATT       240
Asn Asp Lys Gly Ile Gln Thr Ser Glu Asp Tyr Arg Phe Tyr Ala Ile
                 65                  70                  75

TCA GCT GAA TTC CCT GAA TTC AGT AAT AAA GAT AAG ACT CTA GTC TTC       288
Ser Ala Glu Phe Pro Glu Phe Ser Asn Lys Asp Lys Thr Leu Val Phe
         80                  85                  90
```

```
CAA TTT TCT GTC AAG CAT GAA CAG AAG CTT GAC TGT GGT GGT GGT TAC         336
Gln Phe Ser Val Lys His Glu Gln Lys Leu Asp Cys Gly Gly Gly Tyr
 95             100                 105                 110

ATG AAG TTG CTC AGT AGT AGC ACT GAC CAG AAG AAA TTT GGT GGT GAC         384
Met Lys Leu Leu Ser Ser Ser Thr Asp Gln Lys Lys Phe Gly Gly Asp
                115                 120                 125

ACT CCA TAC AGT ATC ATG TTT GGA CCC GAT ATA TGT GGC TAC AGC ACC         432
Thr Pro Tyr Ser Ile Met Phe Gly Pro Asp Ile Cys Gly Tyr Ser Thr
        130                 135                 140

AAA AAA GTT CAT GCT ATC CTT AAC TAC AAT GAT ACA AAC CAC TTG ATC         480
Lys Lys Val His Ala Ile Leu Asn Tyr Asn Asp Thr Asn His Leu Ile
            145                 150                 155

AAA AAG GAA GTT CCA TGT GAA ACC GAC CAG TTA ACT CAT GTT TAC ACA         528
Lys Lys Glu Val Pro Cys Glu Thr Asp Gln Leu Thr His Val Tyr Thr
160                 165                 170

TTG GTC ATC CGT CCA GAT GCT ACT TAT AGC ATT CTT ATC GAC AAT GTG         576
Leu Val Ile Arg Pro Asp Ala Thr Tyr Ser Ile Leu Ile Asp Asn Val
175                 180                 185                 190

GAG AAG CAA ACT GGT AGT TTG TAC ACT GAC TGG GAT CTT CTT CCA CCT         624
Glu Lys Gln Thr Gly Ser Leu Tyr Thr Asp Trp Asp Leu Leu Pro Pro
                195                 200                 205

AAG AAA ATT AAG GAC CCT GAG GCC AAG AAA CCA GAA GAT TGG GAT GAG         672
Lys Lys Ile Lys Asp Pro Glu Ala Lys Lys Pro Glu Asp Trp Asp Glu
        210                 215                 220

AAG GAG TAT ATT CCT GAC CCT GAG GAT AAG AAA CCA GAG GGT TAT GAT         720
Lys Glu Tyr Ile Pro Asp Pro Glu Asp Lys Lys Pro Glu Gly Tyr Asp
            225                 230                 235

GAC ATT CCA AAG GAG ATT CCA GAT CCC GAT GCC AAG AAG CCT GAG GAT         768
Asp Ile Pro Lys Glu Ile Pro Asp Pro Asp Ala Lys Lys Pro Glu Asp
240                 245                 250

TGG GAT GAT GAG GAA GAT GGT GAA TGG ACT GCC CCA ACC ATT GCC AAC         816
Trp Asp Asp Glu Glu Asp Gly Glu Trp Thr Ala Pro Thr Ile Ala Asn
255                 260                 265                 270

CCT GAG TAC AAG GGT CCA TGG AAA CCC AAG AAA ATT AAG AAC CCC AAC         864
Pro Glu Tyr Lys Gly Pro Trp Lys Pro Lys Lys Ile Lys Asn Pro Asn
                275                 280                 285

TAC AAG GGC AAG TGG AAA GCA CCA ATG ATC GAC AAC CCA GAT TTC AAG         912
Tyr Lys Gly Lys Trp Lys Ala Pro Met Ile Asp Asn Pro Asp Phe Lys
        290                 295                 300

GAT GAC CCA GAA ATC TAT GTT TAC CCC AAC TTG AAG TAT GTT GGT ATT         960
Asp Asp Pro Glu Ile Tyr Val Tyr Pro Asn Leu Lys Tyr Val Gly Ile
            305                 310                 315

GAA TTG TGG CAG GTG AAA TCT GGA ACC TTG TTT GAC AAT GTC TTG ATT        1008
Glu Leu Trp Gln Val Lys Ser Gly Thr Leu Phe Asp Asn Val Leu Ile
320                 325                 330

TGC AAT GAC CCT GAG TAT GCT AAG CAG CTG GCT GAA GAG ACA TGG GGA        1056
Cys Asn Asp Pro Glu Tyr Ala Lys Gln Leu Ala Glu Glu Thr Trp Gly
335                 340                 345                 350

AAG AAC AAA GAT GCT GAG AAG GCA GCA TTT GAA GAG GCA GAG AAG AAG        1104
Lys Asn Lys Asp Ala Glu Lys Ala Ala Phe Glu Glu Ala Glu Lys Lys
                355                 360                 365

AAA GAA GAG GAG GAA TCA AAG GAT GAT CCA GCT GAT TCT GAT GCT GAC        1152
Lys Glu Glu Glu Glu Ser Lys Asp Asp Pro Ala Asp Ser Asp Ala Asp
        370                 375                 380

GAG GAC GAT GAT GAT GCT GAT GAC ACT GAA GGA GAA GAT GAT GGT GAA        1200
Glu Asp Asp Asp Asp Ala Asp Asp Thr Glu Gly Glu Asp Asp Gly Glu
            385                 390                 395

AGC AAA TCA GAT GCA GCA GAA GAC AGT GCT GAG GAC GTA CAT GAT GAA        1248
Ser Lys Ser Asp Ala Ala Glu Asp Ser Ala Glu Asp Val His Asp Glu
400                 405                 410
```

```
CTG TAGAGAGGAA GCACTTTTGC TGACAAGCGA TGGAGATGAG CGGGGGCATA      1301
Leu
415

TAGTAGTACT CCCAAAATTT TTCTATTTTC TTTTGATTCG TAGCTGTAGG AGCTCTTGTA  1361

GGGAAAGAAA AATAGAGAAA GTTGCACTGC AGAACTGCTT GGCTGATTGT TTTAGTCCCC  1421

ATTTAAAACC TGTCTGAGCC TTTAGAACAA AGAAGATGTC CTTTTATAAT CAAATTTATG  1481

ATTTGAATGT TCTACAAAAA AAAAAAAAAA AAA                              1514
```

(2) INFORMATION FOR SEQ ID NO:2:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Asn Pro Lys Ser Leu Ser Leu Phe Leu Leu Ser Leu Leu Ala
 1               5                  10                  15

Ile Ala Ser Ala Glu Val Phe Phe Glu Glu Arg Phe Glu Asp Gly Trp
                20                  25                  30

Glu Asn Arg Trp Val Lys Ser Asp Trp Lys Asp Glu Asn Thr Ala
             35                  40                  45

Gly Glu Trp Asn Tyr Thr Ser Gly Lys Trp Asn Gly Asp Pro Asn Asp
         50                  55                  60

Lys Gly Ile Gln Thr Ser Glu Asp Tyr Arg Phe Tyr Ala Ile Ser Ala
 65                  70                  75                  80

Glu Phe Pro Glu Phe Ser Asn Lys Asp Lys Thr Leu Val Phe Gln Phe
                 85                  90                  95

Ser Val Lys His Glu Gln Lys Leu Asp Cys Gly Gly Tyr Met Lys
                100                 105                 110

Leu Leu Ser Ser Ser Thr Asp Gln Lys Lys Phe Gly Gly Asp Thr Pro
            115                 120                 125

Tyr Ser Ile Met Phe Gly Pro Asp Ile Cys Gly Tyr Ser Thr Lys Lys
        130                 135                 140

Val His Ala Ile Leu Asn Tyr Asn Asp Thr Asn His Leu Ile Lys Lys
145                 150                 155                 160

Glu Val Pro Cys Glu Thr Asp Gln Leu Thr His Val Tyr Thr Leu Val
                165                 170                 175

Ile Arg Pro Asp Ala Thr Tyr Ser Ile Leu Ile Asp Asn Val Glu Lys
            180                 185                 190

Gln Thr Gly Ser Leu Tyr Thr Asp Trp Asp Leu Leu Pro Pro Lys Lys
        195                 200                 205

Ile Lys Asp Pro Glu Ala Lys Lys Pro Glu Asp Trp Asp Glu Lys Glu
    210                 215                 220

Tyr Ile Pro Asp Pro Glu Asp Lys Lys Pro Glu Gly Tyr Asp Asp Ile
225                 230                 235                 240

Pro Lys Glu Ile Pro Asp Pro Asp Ala Lys Lys Pro Glu Asp Trp Asp
                245                 250                 255

Asp Glu Glu Asp Gly Glu Trp Thr Ala Pro Thr Ile Ala Asn Pro Glu
            260                 265                 270

Tyr Lys Gly Pro Trp Lys Pro Lys Lys Ile Lys Asn Pro Asn Tyr Lys
        275                 280                 285
```

```
Gly Lys Trp Lys Ala Pro Met Ile Asp Asn Pro Asp Phe Lys Asp Asp
    290                 295                 300
Pro Glu Ile Tyr Val Tyr Pro Asn Leu Lys Tyr Val Gly Ile Glu Leu
305                 310                 315                 320
Trp Gln Val Lys Ser Gly Thr Leu Phe Asp Asn Val Leu Ile Cys Asn
                325                 330                 335
Asp Pro Glu Tyr Ala Lys Gln Leu Ala Glu Thr Trp Gly Lys Asn
            340                 345                 350
Lys Asp Ala Glu Lys Ala Ala Phe Glu Glu Ala Glu Lys Lys Glu
        355                 360                 365
Glu Glu Glu Ser Lys Asp Asp Pro Ala Asp Ser Asp Ala Asp Glu Asp
    370                 375                 380
Asp Asp Asp Ala Asp Asp Thr Glu Gly Glu Asp Gly Glu Ser Lys
385                 390                 395                 400
Ser Asp Ala Ala Glu Asp Ser Ala Glu Asp Val His Asp Glu Leu
            405                 410                 415
```

(2) INFORMATION FOR SEQ ID NO:3:

(i) SEQUENCE CHARACTERISTICS:
        (A) LENGTH: 3191 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
ACCGGTAATA CCGAAGAAGA AGATCTGCTA TAAATAACGC TCTCACTCTC TTACTCTACA      60
GCTCCAAAAT TCTCTCTCTA GAAATGGCGA ACCCTAAATC TCTCTCACTC TTTCTTCTCT     120
CGCTTTTAGC GATCGCTTCT GCAGAAGTCT TCTTCGAGGA GCGTTTCGAA GGTATCTATC     180
CATCTTACTT TAACACTGTC CATACGTCGT CTTTATGATT ACTTTCTTCT TGTGTTTTTA     240
TTCCGTGGAT CTATTTGCTT TTAACTGTTT CTTTGCTTAT CGCGTAATTA AGGATAGAAC     300
TGTAATTAGT TTTGATAGAT CTGTTAATAA TGTTTGGTTT TGCTTTCGGC AATGATGATT     360
GATCAGAAAT TAGAAATGGA ACTCCTGGTT TGTGTTTGCT TGTTGAGAAA AGAATGCGAT     420
CAGGTGTTAA TGTACTGGAT TGATCGAGCA TTTGTTTAGA TCTGTTTGGA TAATGTGTTT     480
TTGTGATAAT TCGTGAGAAA TGGTCGTGTT TGATTATATG AAATTTAAAT TTTGGAAAAT     540
TAGTAATTAC ACGTGCATAT TTTCATTAGC CGGAATTGGT CAAAGTTTGA CTCTCTATTT     600
GTTTTCAGCG TTAGCCTTTT CTAACTAAAA AGCACATTTG ATTGTACCTT TCTTGAAATT     660
TTACCGTTTA TATTTCAGTT TGCATAACTT TGCTTAGTGA AACTGAACAG TAAAATTAAG     720
TATGCATAAT CCAACAATTG CTAATTACAT TTCTGTTTTA CTGGTTTGCA GATGGATGGG     780
AAAATAGGTG GGTAAATCT GATTGGAAGA AAGATGAGAA TACAGCTGGT GAATGGAATT     840
ATACCTCTGG AAAGTGGAAT GGAGACCCTA ATGACAAAGG TATGATTGTT TGCTCAACAA     900
ATACTAACTA TTTGAGAGTT TCCAAATAAA ATTTCTTTTA GCTGTTGTAC GATTTTAATG     960
ATTTTAACAT CTTGATGCAG GTATTCAAAC AAGTGAAGAT TATAGGTTCT ATGCTATTTC    1020
AGCTGAATTC CCTGAATTCA GTAATAAAGA TAAGACTCTA GTCTTCCAAT TTTCTGTCAA    1080
GCATGAACAG AAGCTTGACT GTGGTGGTGG TTACATGAAG TTGCTCAGTA GTAGCACTGA    1140
```

-continued

| | |
|---|---|
| CCAGAAGAAA TTTGGTGGTG ACACTCCATA CAGGTGAGGA CAGTTTACGG TTTTAATTTT | 1200 |
| GTGTTTTTTC TTTTTAGTTC TTCTAATGAA ATACTAACTG GTTATCTTTT TTGGTTGACT | 1260 |
| TCAGTATCAT GTTTGGACCC GATATATGTG GCTACAGCAC CAAAAAAGTT CATGCTATCC | 1320 |
| TTAACTACAA TGATACAAAC CACTTGATCA AAAAGGAAGT TCCATGTGAA ACCGACCAGT | 1380 |
| TAACTCATGT TTACACATTG GTCATCCGTC CAGATGCTAC TTATAGCATT CTTATCGACA | 1440 |
| ATGTGGAGAA GCAAACTGGT AGTTTGTACA CTGACTGGGA TCTTCTTCCA CCTAAGAAAA | 1500 |
| TTAAGGACCC TGAGGCCAAG AAAGTAATCA CTTTGCACTT TAATTCTTCT AACATTGTAC | 1560 |
| TGGCATTTGA GTTTTGGTGG TTACTCAACT TTTAAACTTG ATGGCAGCCA GAAGATTGGG | 1620 |
| ATGAGAAGGA GTATATTCCT GACCCTGAGG ATAAGAAACC AGAGGTAATG ACATGTCAAA | 1680 |
| TCACCTAGTC TGCCTGGTTC ACGCCATATT TTCTAGTGAC AACAAAAATG TATATCTGAA | 1740 |
| GCTAATGTTT TTCTTCTGTT TCTTTTAGGG TTATGATGAC ATTCCAAAGG AGATTCCAGA | 1800 |
| TCCCGATGCC AAGAAGGTAG ATATATTGAA ATTCTTGTGT TTGTTTCTAC TGCACCTTTA | 1860 |
| TTTGGTAGAA AAGTAGATTC TGATGAAGGT GGCTTACAAT TGTAGCCTGA GGATTGGGAT | 1920 |
| GATGAGGAAG ATGGTGAATG GACTGCCCCA ACCATTGCCA ACCCTGAGTA CAAGGGTCCA | 1980 |
| TGGAAACCCA AGGTCTGTGG TTTATGATCA AGTTGCAGCC TCTGCTATCC AATGTGTAAT | 2040 |
| TTGGAGCCAT AACTTATGCG ATTTTGTTCT TTTTGCAGAA AATTAAGAAC CCCAACTACA | 2100 |
| AGGGCAAGTG GAAAGCACCA ATGATCGACA ACCCAGATTT CAAGGATGAC CCAGAAATCT | 2160 |
| ATGTTTACCC CAACTTGAAG TATGTTGGTA TTGAATTGTG GCAGGTAATT TTCTTTCCAT | 2220 |
| ATTTTATCTA GTTGTTTGAA TTTGCCCGGT GACTAACAAA ACAAATCCCA CTATTGTGTC | 2280 |
| AGGTGAAATC TGGAACCTTG TTTGACAATG TCTTGATTTG CAATGACCCT GAGTATGCTA | 2340 |
| AGCAGCTGGC TGAAGAGACA TGGGGAAAGA ACAAAGATGT ATGTGGCCTT TGCATATTTA | 2400 |
| AATTATAATC TTCAAAAAAG ACTCTTGTCT CGATACTTTA CTGAGATTGT CAAATTTCAG | 2460 |
| GCTGAGAAGG CAGCATTTGA AGAGGCAGAG AAGAAGAAAG AAGAGGAGGT ACTTCCTTTC | 2520 |
| TCATAAATTG CAGTTTGAAT TTGAATGGCT TTTCTTGGAT GGAATTAGCT AGAGAGGTTC | 2580 |
| TGATGCTGCA AATAGCTAAC TCATAGGTTT AAATTTTTTC AGGAATCAAA GGATGATCCA | 2640 |
| GCTGATTCTG ATGTAAGCCT GCGAACTGTT TCCTGAAACA AATTTAGTTT GTTTCTGTGA | 2700 |
| CTTTTACCTA ATTGAACCAT TTTTTTCAGG CTGACGAGGA CGATGATGAT GCTGATGACA | 2760 |
| CTGAAGGAGA AGATGATGGT GAAAGCAAAT CAGATGCAGC AGAAGACAGT GCTGAGGACG | 2820 |
| TACATGTAAA TTCTCTAACT TTTATGATTG TGGTAACTGG TAAAGAAGCA TTTAATTTGT | 2880 |
| GTGCACTGAT AAAATTTGTC AATTGTGTTG TGTTGGCAGG ATGAACTGTA GAGAGGAAGC | 2940 |
| ACTTTTGCTG ACAAGCGATG GAGATGAGCG GGGGCATATA GTAGTACTCC CAAAATTTTT | 3000 |
| CTATTTTCTT TTGATTCGTA GCTGTAGGAG CTCTTGTAGG GAAAGAAAAA TAGAGAAAGT | 3060 |
| TGCACTGCAG AACTGCTTGG CTGATTGTTT TAGTCCCCAT TTAAAACCTG TCTGAGCCTT | 3120 |
| TAGAACAAAG AAGATGTCCT TTTATAATCA AATTTATGAT TTGAATGTTC TACAAAAAAA | 3180 |
| AAAAAAAAA A | 3191 |

(2) INFORMATION FOR SEQ ID NO:4:

(i) SEQUENCE CHARACTERISTICS:
        (A) LENGTH: 1928 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

| | | | | | |
|---|---|---|---|---|---|
| GCATGCTAAA | TCACTAGGTC | CTAAAGGTTC | AGACCCTCAC | AAAGCTGCTG | TCATTGGCGA | 60 |
| CACAATCGGC | GACCCTCTTA | AGGACACTTC | GGGTCCATCA | CTTAATATCC | TGATCAAGCT | 120 |
| CATGGCAGTC | GAGTCATTGG | TGTTTGCTCC | ATTCTTTGCT | GCTCACGGAG | GTCTGCTGTT | 180 |
| CAAATTGCTG | TAATTTAAGC | AAGCAAGTTA | TAACCCGAGC | AAAGATATGT | TGTTACGACG | 240 |
| GAAGCAATAT | CATGTAATTG | AGTTCTCACT | GTTATAGTTT | CAACATGTAA | AAAGAATATA | 300 |
| AAAAAAGAAA | CAGATATATG | GCTTTGCTGC | TTCTACATTG | CTAAATTTAC | CGTGAATAAA | 360 |
| ATTGTAGTTT | CATATATACA | TTTCTTCCTT | TTGCAGTCTA | GCATTGGCCT | TAATAACACC | 420 |
| GATTCACAAC | TGGAACTGAA | CTAGCCGTTT | TGGAGGCTTG | GCTTGTCTTA | CTAAGGGGTT | 480 |
| CCCACATGAC | ACCCATTAGA | GACTGAACGT | AAACCTTAGA | TTAATGGCAA | TTTGCAAGAT | 540 |
| ATGTAAATGC | AATGACACAC | CCAAAATCAT | ATAGACGAGG | TTAACTAATG | TTTCAAATTC | 600 |
| GAACTTTGAA | ATGCATTTAC | ATTATAATTT | TTGAAAAAGT | ATTTTATCAT | CTCCAAGTAT | 660 |
| CATATTCAGT | AAGTTCTAGG | TACTGCTTTC | TCCATATATA | TATTCCATAC | TCGGGTAAAT | 720 |
| TGTAGATTAA | CTATATATAT | ATATATTTTG | TAAAGACAGT | GGCTGACCCG | TCACCCTATG | 780 |
| CTCTAACCTT | AATGATTCGC | TTCAAACGCA | AGCATCCAAA | TCAGCCAATA | AAAGTAAGTG | 840 |
| CCGGCCCCCA | CTTTTCTGAC | AGAAATTATT | ATGCAAGTGT | ACAACAACAA | GGCCTACTGA | 900 |
| AAATCATCAC | TTGTGGTGGA | CTTTAGTACC | TTGTTTAAGC | ATACTCATTT | GTTATTATAC | 960 |
| CCATAACAAG | AACCCTATCC | CTAATTGCAT | AGATTCTTAT | TTATTTAAGG | GAATGAAATG | 1020 |
| TCATGAACTG | AATTCTTAAT | TATTTCCTTT | TTTCTTTTTG | CTTAACATAT | TTGAATTATA | 1080 |
| CCACAAAGGG | TAATTTTTAA | TTTTTTAGAT | AGTTAGATTA | TCTTTAAAGG | TTGTATTATA | 1140 |
| AAAATAATAA | ATTTCCATTA | ATATCAACTG | GTGGTATATA | AGAAAACACT | TTGAAATTCT | 1200 |
| TGTAATTTTC | ACAGATATTT | AGTTTTTTTT | TTTTAAAAAA | TTTGTTTTAG | ATAAAACATA | 1260 |
| ATTAATCTTA | CTTTTTCAAA | AATAATCTAT | TAGAAAATTT | TTAAATCTGT | TTCTTCCTTT | 1320 |
| TTAATACTCA | ACCAATAATT | TTAAACATTA | ACGCCACTAG | TGTATTGCTT | TTTACCTTAA | 1380 |
| TAGATGATTC | TAGAGAATTA | ATTTCTAATT | CTTAATTAAA | CATATAGCCA | AATCCGGAAC | 1440 |
| CCTATTAAAA | CCCTTCTAAT | TTTATTATTA | TCTATATGAG | GAAATCACAA | GCAACCTTTT | 1500 |
| CATCAGGCTG | GGTCCACAAT | TACCAATCAC | CCCTCATAGC | ACGCCACGTG | TCACTCAATT | 1560 |
| TTCAGTAACA | GAATAAACAC | ATAAAAGGCC | ATTCTTAATC | CAAATACGAT | ATTACCACGT | 1620 |
| GTAAAATACT | ACTTGCCCTC | TACAATTCGT | GGAATCTCCC | AATCGTATTA | TGCCATGTCA | 1680 |
| TACTAATGAC | ACTTCAATCC | GAGTTGCCGA | TATACTATTA | GTCCACGTAA | CTGGATGTTG | 1740 |
| TCCAGCTAGG | ATGTTTACCC | ATAGTAAAAT | ACATATTTTA | ACTAACCGGT | AATACCGAAG | 1800 |
| AAGAAGATCT | GCTATAAATA | ACGCTCTCAC | TCTCTTACTC | TACAGCTCCA | AAATTCTCTC | 1860 |
| TCTAGAAATG | GCGAACCCTA | AATCTCTCTC | ACTCTTTCTT | CTCTCGCTTT | TAGCGATCGC | 1920 |
| TTCTGCAG | | | | | | 1928 |

(2) INFORMATION FOR SEQ ID NO:5:

(i) SEQUENCE CHARACTERISTICS:
        (A) LENGTH: 2072 base pairs (B) TYPE: nucleic acid
(C) STRANDEDNESS: single
(D) TOPOLOGY: linear (ii) MOLECULE TYPE: DNA (cDNA)

(iii) HYPOTHETICAL: NO (iv) ANTI-SENSE: NO (xi) SEQUENCE DESCRIPTION: SEQ ID NO:5:

```
GGCACGAGCT TGTGTTAGAT TAGATTTTAG ATTCAGATCA GATCAATAAT TATACTTAGC      60
TAAACCTAGG AGGAGTAGCT AGGGTTTTGA GAGTTTTTGG GATACCAAGA GATGGGAGAA     120
GCAAAACGCA TCTCTCTACG ATTAGCTCTT GTATTTTTAG TAGCTTTTGT TTCCTTCGTT     180
CAGCTACGAG CAGACTCTGA CGATAATAAG ATCTTCTACG AGTCATTTGA GGACTCATTT     240
GAAGGACGAT GGACTCTGTC TGCTAAAGAT GACTACAAAG GTGAGTGGAA GCACGCGAAG     300
AGTGAAGGTC ATGATGAGTA TGGCCTTCTT GTGAGTGAAA AAGCTAGGAA GTATGCCATT     360
GTGAAAGAGC TCGACGAACC GGCAACTCTC AAGGATGGAA CCATTGTTCT CCAATTCGAG     420
ACTCGTTTTC AGAATGGGCT TGAATGCGGT GGCGCATATC TTAAATATTT GCGTCCCCAG     480
GAAGCTGGGT GGACTCCTAA GGATTTTGAC AATGACTCTC CTTATTCTAT AATGTTTGGA     540
CCTGACAAAT GTGGGCCAC AAACAAGGTG CACTTCATTC TTAAGCACAA GAACCCAAAG      600
AGTGGCGAGT ACATTGAACA CCATCTCAAA TATCCACCAT CTGTTCCATC TGACAAACTC     660
ACCCATGTCT ATACTGCCAT TCTGAAACCT GACAATGAGC TGCGAATTTT GGTTGATGGA     720
GAAGAGAAGA AGAAGGCAAA TTTTCTCTCA TCTGATGATT TCGAGCCTCC TTTAGTTCCT     780
GCCAAGACAA TTCCTGATCC GGATGATAAG AAGCCTGAAG ACTGGGATGA GCGAGCCAAA     840
ATTCCTGATC CTAATGCAGT GAAGCCAGAT GATTGGGACG AGGATGCACC TATGGAAATT     900
GTAGATGAGG ATGCTGAGAA ACCTGAAGGA TGGTTAGATG ATGAGCCTGA GGAAATTGAT     960
GATCCTGATG CTGCAAAACC TGAAGATTGG GATGATGAGG AGGATGGTGA ATGGGAGGCA    1020
CCAAAGATTG ATAACCCAAA GTGTGAGACA GCACCTGGTT GTGGTGAATG GAAGAGGCCA    1080
ATGAAAAGAA ATCCAGCTTA CAAAGGAAAA TGGCATGCTC CACTTATTGA CAACCCCAAC    1140
TATAAGGGTA TCTGGAAGCC TCAGGAGATT CCAAACCCCA ACTACTTTGA GCTTGAAAAG    1200
CCTGACTTTG AGCCCATTGC TGCTGTTGGC ATTGAGATCT GGACAATGCA GGACGGTATT    1260
TTGTTTGGAC ATATCTTGAT AGCAGATGAT GAGAAGGTTG CAGAGTCACT CAGGCAGACA    1320
GCATGGAAGC CAAAGTTTGA TGCTGAGAAA GAGAAACAGA AGGCTGAGGA TGCAGCTGCT    1380
GGTTCAGATG GTCTTGCTGG CTTCCAGAAG AAGGTGTTTG ATCTGCTGTA CCAGGTTGCA    1440
GATATTCCTT TCTTAAGCGA GCACAAGGAC AAAATTATTG ATATTATTGA AAAGGGAGAG    1500
AAACAGCCCA ACCTCACAAT TGGTATACTC GTCTCCATTG TGGTGGTGAT CTTTACTGTG    1560
CTTTTTAAGA TCCTCTTTGG TGGGAAGAAG CCTGCAAAAG TAGAAGAGAA ACCTGCACCA    1620
GCTGCTGAGA CTTCGAAAAA GGAAGAAAGC AGTGGAGAGA AAGCGGAAGA GAACGAGAAG    1680
GAAGATGCTG CAGCTGCTGC TGCTCCCCCT CGCAGAAGGC AAGCCAGGCG CGAGAACTAA    1740
AAGGACAATG AAAGGAGAGT GGTCCGCTTC AACTTTCACT TTTGGTAGAT CTTCAGTTTA    1800
GGCGTCTTTA CACTCTTGCT GGCTGGATTC TTGCATATCT CTCTTTTTTT TCTTTCTTTT    1860
CTTGTTCGGG TTTTGTGGCT CTGTTTTGGA GCATAAAATG GATGAAGAGT GTAAATGACA    1920
TGATGATCTG TGAGGTTTTG ATACTTCATT TCCCGCCTCG GAAGTAAAAT TAGCCTGCCA    1980
ACTTAAGGAT ATTATTGTTG ATTTGACTAT TAAAGAAAAC ACATGCAACT AATGTGAAAG    2040
```

TAGCATTTTT ATTTAAAAAA AAAAAAAAAA AA                                                    2072

(2) INFORMATION FOR SEQ ID NO:6:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Glu Ala Lys Arg Ile Ser Leu Arg Leu Ala Leu Val Phe Leu
1               5                   10                  15

Val Ala Phe Val Ser Phe Val Gln Leu Arg Ala Asp Ser Asp Asp Asn
            20                  25                  30

Lys Ile Phe Tyr Glu Ser Phe Glu Asp Ser Phe Glu Gly Arg Trp Thr
        35                  40                  45

Leu Ser Ala Lys Asp Asp Tyr Lys Gly Glu Trp Lys His Ala Lys Ser
    50                  55                  60

Glu Gly His Asp Glu Tyr Gly Leu Leu Val Ser Glu Lys Ala Arg Lys
65                  70                  75                  80

Tyr Ala Ile Val Lys Glu Leu Asp Glu Pro Ala Thr Leu Lys Asp Gly
                85                  90                  95

Thr Ile Val Leu Gln Phe Glu Thr Arg Phe Gln Asn Gly Leu Glu Cys
            100                 105                 110

Gly Gly Ala Tyr Leu Lys Tyr Leu Arg Pro Gln Glu Ala Gly Trp Thr
        115                 120                 125

Pro Lys Asp Phe Asp Asn Asp Ser Pro Tyr Ser Ile Met Phe Gly Pro
    130                 135                 140

Asp Lys Cys Gly Ala Thr Asn Lys Val His Phe Ile Leu Lys His Lys
145                 150                 155                 160

Asn Pro Lys Ser Gly Glu Tyr Ile Glu His His Leu Lys Tyr Pro Pro
                165                 170                 175

Ser Val Pro Ser Asp Lys Leu Thr His Val Tyr Thr Ala Ile Leu Lys
            180                 185                 190

Pro Asp Asn Glu Leu Arg Ile Leu Val Asp Gly Glu Glu Lys Lys Lys
        195                 200                 205

Ala Asn Phe Leu Ser Ser Asp Asp Phe Glu Pro Pro Leu Val Pro Ala
    210                 215                 220

Lys Thr Ile Pro Asp Pro Asp Lys Lys Pro Glu Asp Trp Asp Glu
225                 230                 235                 240

Arg Ala Lys Ile Pro Asp Pro Asn Ala Val Lys Pro Asp Asp Trp Asp
                245                 250                 255

Glu Asp Ala Pro Met Glu Ile Val Asp Glu Asp Ala Glu Lys Pro Glu
            260                 265                 270

Gly Trp Leu Asp Asp Glu Pro Glu Ile Asp Asp Pro Asp Ala Ala
        275                 280                 285

Lys Pro Glu Asp Trp Asp Asp Glu Asp Gly Glu Trp Glu Ala Pro
    290                 295                 300

Lys Ile Asp Asn Pro Lys Cys Glu Thr Ala Pro Gly Cys Gly Glu Trp
305                 310                 315                 320

Lys Arg Pro Met Lys Arg Asn Pro Ala Tyr Lys Gly Lys Trp His Ala
                325                 330                 335

Pro Leu Ile Asp Asn Pro Asn Tyr Lys Gly Ile Trp Lys Pro Gln Glu
```

```
                340              345              350
Ile Pro Asn Pro Asn Tyr Phe Glu Leu Glu Lys Pro Asp Phe Glu Pro
            355              360              365
Ile Ala Ala Val Gly Ile Glu Ile Trp Thr Met Gln Asp Gly Ile Leu
        370              375              380
Phe Gly His Ile Leu Ile Ala Asp Asp Glu Lys Val Ala Glu Ser Leu
385              390              395              400
Arg Gln Thr Ala Trp Lys Pro Lys Phe Asp Ala Glu Lys Glu Lys Gln
                405              410              415
Lys Ala Glu Asp Ala Ala Gly Ser Asp Gly Leu Ala Gly Phe Gln
            420              425              430
Lys Lys Val Phe Asp Leu Leu Tyr Gln Val Ala Asp Ile Pro Phe Leu
        435              440              445
Ser Glu His Lys Asp Lys Ile Ile Asp Ile Ile Glu Lys Gly Glu Lys
    450              455              460
Gln Pro Asn Leu Thr Ile Gly Ile Leu Val Ser Ile Val Val Val Ile
465              470              475              480
Phe Thr Val Leu Phe Lys Ile Leu Phe Gly Gly Lys Lys Pro Ala Lys
                485              490              495
Val Glu Glu Lys Pro Ala Pro Ala Ala Glu Thr Ser Lys Lys Glu Glu
            500              505              510
Ser Ser Gly Glu Lys Ala Glu Glu Asn Glu Lys Glu Asp Ala Ala Ala
        515              520              525
Ala Ala Ala Pro Pro Arg Arg Arg Gln Ala Arg Arg Glu Asn
    530              535              540
```

(2) INFORMATION FOR SEQ ID NO:7:

(i) SEQUENCE CHARACTERISTICS:
        (A) LENGTH: 4358 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
GCATGCTGGC AAGAGTTCAA CTCCTGCCAA CTTTATTCTC CTTGAAATTA ATCAGGTAAA      60
CCATAATAGT GATTCTGTGA AATTAAAGTG TGGTTGGGGT TAAGAACTAA GCATTCCACT     120
AACTAGAAAC AATCGCAGGT TAACAAGCAC CACAACGATC GTTGGAAGAA AATTCACTCC     180
CCGAGCTAGC TAGCCAAATT TGCGAGAAGC TCGACTGCTT CATCTCCCTT GCAGATGATG     240
TTCATATGTG GAATTCACCT CCCACCACTG CCACTGCCAA ACATCCAGC  GCAAGTACCC     300
GAGTCGCCAC ACTTGAGCCA CTTTTACATT ATATAGATAA ATGTATATTG CACCATCCAT     360
GGCATGAAAG CTAGATGAAG TGCATCCGAT ATGAGGCTTG AGAACAGAAC CATGAGATAG     420
ATTCGCAAAT CTCAACCATT GCATGTACTG TTGGCACAGT GGAGTTTGCT TATGTCCTTG     480
AAACACCAAG GAAGCTAATC ATTTTGATTA ATTTTCATTT CGCGTTATTC TATATTCTCT     540
TTTAATTAGT TCTTAAGCAA CCACTATTAT GATACAATGT ACATGTCTAA TCTGATTTAT     600
TTATGCAATC AAAAAATTTA TTCGGAAAAT TCTTGTATAC ACCAAACCAA ATATATATAT     660
ACGTATGTAT AAATATTTAT AATACTTGAT TTTTTTAAA ATATAATTTT TTTATGAAAT     720
```

```
TAAAATTTAA ATAATTACTT ACAGTTCTAA TTAAAATACT TTATTTTATA TTACAATTTT        780

ATTATTTATA AATTCAATAA GTTAATCCCT TAGTAGTTAA TAATTTTTTT ATTCTACCAT        840

ATATATTACT CATAAAAGAT TTCGACTATA TAGAGATATG GAATTTGAAG TCTTTTCTCA        900

TTAGTGGGCG ATCCGATAGT GCACCAATAA ACGAATATCA GACCCAAAAA CCATGGGCTT        960

GGCCAATAAA ACGAAAGCAA CATAACAGTT GAGACTTGGG ACCGGGTCAA GCCCGCAAGT       1020

GTAAAAACAA ATATTCCACC GAAGTAACAT ATGAGAATTG CTGGAGTTGC TTACTTGTCG       1080

AACTCCGATT GGTTGGATTC ACGTGGCACG TAAATTGATT GGCGGAAACA ACACGAAGGC       1140

AGTGATTTCC AAGATCTTTA AGTATACACG CATCGCAAAA TGTAGCAAAA CCAAATCTGT       1200

TAATCTAGAA GTTGTTTTTC CTTTTCTTTC CTTTCCTTTC CTTTCCTTGC CTTGTGTTAG       1260

ATTAGATTTT AGATTCAGAT CAGATCAATA ATTATACTTA GCTAAACCTA GGAGGAGTAG       1320

CTAGGGTTTT GAGAGTTTTT GGGATACCAA GAGATGGGAG AAGCAAAACG CATCTCTCTA       1380

CGATTAGCTC TTGTATTTTT AGTAGCTTTT GTTTCCTTCG TTCAGCTACG AGCAGACTCT       1440

GACGATAATA AGGTAATTAA TCAATTACTT AATTGGTTAA TTGACATTTC TATTTTTGAG       1500

TTTTATGTGA TAATAAAAGA GTGATTTTTG TTTGATATAG ATCTTCTACG AGTCATTTGA       1560

GGACTCATTT GAAGGACGAT GGACTCTGTC TGCTAAAGAT GACTACAAAG GTATATAGTT       1620

ATATTGTGTA TTCTTTTGGA TCTAAATTTT TGCTGTCTAT TTTTTATTTG TTAATTTTAT       1680

TGTTTTTACT GTTGTATTGT TTGTGCTTTC CTTTGGAGTT TGGTTTTTAC TTGCTTATTT       1740

GGTGGTATTG CTGCTGTACT TCTGGAAGTG ATTTGGATAT GGTTTATTTC TAGGTTGTTT       1800

TTTTTCCTCG TGCAACTGAT TGTCTGATGT AGAAATGAAA TTGTTTTGAT ATCATTTTGA       1860

TACTTGAATT CCAGTAGATC AAAGAAATTA TATTTTCAAT TAACTTTTCC TGGATAGTAG       1920

GCGATGTTAC TTGTTAGTTG AAATGTATAT GTAGAGAGAG ATAATTATGA AAATGATAAT       1980

TAGGGTGAGT GGTTGATTTT CGGTTGCAAT TGTGAAAATT GAATAAGTTG TAATAATTAG       2040

GGTAAGTGGT CCTGTCTTTT TCTTGACTTG GAATCTGGAG TTTAAAGAAG ATACTATAAT       2100

TTTGTTATAG TTCTAATAAC CATGACTGAC TGCATTGTAA TCTTGCTACA TGTCTGTTTT       2160

AAATGAATAG AAGGAACTGT TGTTTGTCTA TATTTATATT CTTTTATAAG CTGAGTTTAG       2220

TTGGTTGTCT CTGTCAATTT ATTGTCGGCT GTTTTCTTGA GGTAGAAGCA GATATTGATG       2280

TTTTTATATT GTTTATAGGT GAGTGGAAGC ACGCGAAGAG TGAAGGTCAT GATGAGTATG       2340

GCCTTCTTGT GAGTGAAAAA GCTAGGAAGT ATGCCATTGT GAAAGAGCTC GACGAACCGG       2400

CAACTCTCAA GGATGGAACC ATTGTTCTCC AATTCGAGAC TCGTTTTCAG AATGGGCTTG       2460

AATGCGGTGG CGCATATCTT AAATATTTGC GTCCCCAGGA AGCTGGGTGG ACTCCTAAGG       2520

ATTTTGACAA TGACTCTCCT TATTCTATAA TGTTTGGACC TGACAAATGT GGGGCCACAA       2580

ACAAGGTGCA CTTCATTCTT AAGCACAAGA ACCCAAAGAG TGGCGAGTAC ATTGAACACC       2640

ATCTCAAATA TCCACCATCT GTTCCATCTG ACAAACTCAC CCATGTCTAT ACTGCCATTC       2700

TGAAACCTGA CAATGAGCTG CGAATTTTGG TTGATGGAGA AGAGAAGAAG AAGGCAAATT       2760

TTCTCTCATC TGATGATTTC GAGCCTCCTT TAGTTCCTGC CAAGACAATT CCTGATCCGG       2820

ATGATAAGAA GCCTGAAGAC TGGGATGAGC GAGCCAAAAT TCCTGATCCT AATGCAGTGA       2880

AGCCAGATGA TTGGGACGAG GATGCACCTA TGGAAATTGT AGATGAGGAT GCTGAGAAAC       2940

CTGAAGGATG GTTAGATGAT GAGCCTGAGG AAATTGATGA TCCTGATGCT GCAAAACCTG       3000

AAGATTGGGA TGATGAGGAG GATGGTGAAT GGGAGGCACC AAAGATTGAT AACCCAAAGT       3060

GTGAGACAGC ACCTGGTTGT GGTGAATGGA AGAGGCCAAT GAAAAGAAAT CCAGCTTACA       3120
```

```
AAGGAAAATG GCATGCTCCA CTTATTGACA ACCCCAACTA TAAGGGTATC TGGAAGCCTC    3180

AGGAGATTCC AAACCCCAAC TACTTTGAGC TTGAAAAGCC TGACTTTGAG CCCATTGCTG    3240

CTGTTGGCAT TGAGATCTGG ACAATGCAGG ACGGTATTTT GTTTGGACAT ATCTTGATAG    3300

CAGATGATGA GAAGGTTGCA GAGTCACTCA GGCAGACAGC ATGGAAGCCA AAGTTTGATG    3360

CTGAGAAAGA GAAACAGAAG GCTGAGGATG CAGCTGCTGG TTCAGATGGT CTTGCTGGCT    3420

TCCAGGTAAA TTGATAGCAG TCTTTGTTTT TCATAGATCT TTTGCCTTTT GTAGCTTCTT    3480

GACCTGAGCA TTCTATTTAA TTCTGCAGAA GAAGGTGTTT GATCTGCTGT ACCAGGTTGC    3540

AGATATTCCT TTCTTAAGCG AGCACAAGGA CAAAATTATT GTAAGTTTTA AAAATTATAT    3600

ATGCTGTCAA AATTTTGGTA GGCATTGTGG TGGATGTGGG CTGAGTTTGT GTGCATGTTT    3660

CTGTAGGATA TTATTGAAAA GGGAGAGAAA CAGCCCAACC TCACAATTGG TATACTCGTC    3720

TCCATTGTGG TGGTGATCTT TACTGTGCTT TTTAAGATCC TCTTTGGTGG GAAGAAGCCT    3780

GTAAGTTCCA AAAACTCTC ACTGCGCTAG TATTTATCCA TTCTTATGTT TGCTGCTTAT    3840

CTGGGAGTTT AGCAGGCAAT GATTTTCTC ATTGTATTTT GCTAACAATA TATGTAGGCA    3900

AAAGTAGAAG AGAAACCTGC ACCAGCTGCT GAGACTTCGA AAAAGGAAGA AAGCAGTGGA    3960

GAGAAAGCGG AAGAGAACGA GAAGGAAGAT GCTGCAGCTG CTGCTGCTCC CCCTCGCAGA    4020

AGGCAAGCCA GGCGCGAGAA CTAAAAGGAC AATGAAAGGA GAGTGGTCCG CTTCAACTTT    4080

CACTTTTGGT AGATCTTCAG TTTAGGCGTC TTTACACTCT TGCTGGCTGG ATTCTTGCAT    4140

ATCTCTCTTT TTTTCTTTCT TTTCTTGTTC GGGTTTTGTG GCTCTGTTTT GGAGCATAAA    4200

ATGGATGAAG AGTGTAAATG ACATGATGAT CTGTGAGGTT TTGATACTTC ATTTCCCGCC    4260

TCGGAAGTAA AATTAGCCTG CCAACTTAAG GATATTATTG TTGATTTGAC TATTAAAGAA    4320

AACACATGCA ACTAATGTGA AAGTAGCATT TTTATTTA                           4358

(2) INFORMATION FOR SEQ ID NO:8:

(i) SEQUENCE CHARACTERISTICS:
        (A) LENGTH: 1356 base pairs
        (B) TYPE: nucleic acid
        (C) STRANDEDNESS: single
        (D) TOPOLOGY: linear (xi) SEQUENCE DESCRIPTION: SEQ ID NO:8:

GCATGCTGGC AAGAGTTCAA CTCCTGCCAA CTTTATTCTC CTTGAAATTA ATCAGGTAAA     60

CCATAATAGT GATTCTGTGA AATTAAAGTG TGGTTGGGGT TAAGAACTAA GCATTCCACT    120

AACTAGAAAC AATCGCAGGT TAACAAGCAC CACAACGATC GTTGGAAGAA AATTCACTCC    180

CCGAGCTAGC TAGCCAAATT TGCGAGAAGC TCGACTGCTT CATCTCCCTT GCAGATGATG    240

TTCATATGTG GAATTCACCT CCCACCACTG CCACTGCCAA ACATCCAGC GCAAGTACCC     300

GAGTCGCCAC ACTTGAGCCA CTTTTACATT ATATAGATAA ATGTATATTG CACCATCCAT    360

GGCATGAAAG CTAGATGAAG TGCATCCGAT ATGAGGCTTG AGAACAGAAC CATGAGATAG    420

ATTCGCAAAT CTCAACCATT GCATGTACTG TTGGCACAGT GGAGTTTGCT TATGTCCTTG    480

AAACACCAAG GAAGCTAATC ATTTTGATTA ATTTTCATTT CGCGTTATTC TATATTCTCT    540

TTTAATTAGT TCTTAAGCAA CCACTATTAT GATACAATGT ACATGTCTAA TCTGATTTAT    600

TTATGCAATC AAAAAATTTA TTCGGAAAAT TCTTGTATAC ACCAAACCAA ATATATATAT    660

ACGTATGTAT AAATATTTAT AATACTTGAT TTTTTTTAAA ATATAATTTT TTTATGAAAT    720

TAAAATTTAA ATAATTACTT ACAGTTCTAA TTAAAATACT TTATTTTATA TTACAATTTT    780
```

```
ATTATTTATA AATTCAATAA GTTAATCCCT TAGTAGTTAA TAATTTTTTT ATTCTACCAT    840

ATATATTACT CATAAAAGAT TTCGACTATA TAGAGATATG GAATTTGAAG TCTTTTCTCA    900

TTAGTGGGCG ATCCGATAGT GCACCAATAA ACGAATATCA GACCCAAAAA CCATGGGCTT    960

GGCCAATAAA ACGAAAGCAA CATAACAGTT GAGACTTGGG ACCGGGTCAA GCCCGCAAGT   1020

GTAAAAACAA ATATTCCACC GAAGTAACAT ATGAGAATTG CTGGAGTTGC TTACTTGTCG   1080

AACTCCGATT GGTTGGATTC ACGTGGCACG TAAATTGATT GGCGGAAACA ACACGAAGGC   1140

AGTGATTTCC AAGATCTTTA AGTATACACG CATCGCAAAA TGTAGCAAAA CCAAATCTGT   1200

TAATCTAGAA GTTGTTTTTC CTTTTCTTTC CTTTCCTTTC CTTTCCTTGC CTTGTGTTAG   1260

ATTAGATTTT AGATTCAGAT CAGATCAATA ATTATACTTA GCTAAACCTA GGAGGAGTAG   1320

CTAGGGTTTT GAGAGTTTTT GGGATACCAA GAGATG                            1356

(2) INFORMATION FOR SEQ ID NO:9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:9:

WCTMACCTAM CM                                                         12

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:10:

TCATCTTCTT                                                            10

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:11:

ATCATTTCNA CT                                                         12

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

NTTCNNGAAN NTTCNNGAAN                                                 20

(2) INFORMATION FOR SEQ ID NO:13:

(i) SEQUENCE CHARACTERISTICS:
        (A) LENGTH: 11 base pairs
        (B) TYPE: nucleic acid
```

```
            (C) STRANDEDNESS: single
            (D) TOPOLOGY: linear (xi) SEQUENCE DESCRIPTION: SEQ ID NO:13:

GCANCATRCR Y                                                                11

(2) INFORMATION FOR SEQ ID NO:14:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:14:

GATGAYRTGR                                                                  10

(2) INFORMATION FOR SEQ ID NO:15:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:15:

TCATCTTCTT                                                                  10

(2) INFORMATION FOR SEQ ID NO:16:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:16:

AAGCGTAAGT                                                                  10
```

CALRETICULIN GENES AND PROMOTER REGIONS AND USES THEREOF

TECHNICAL FIELD

The present invention relates generally to the calcium-binding proteins, calreticulin and calnexin, and more specifically, to their genomic structure, coding regions, and promoter sequences.

BACKGROUND OF THE INVENTION

Plants are subject to assault from a variety of diseases that affect growth, flowering, fruiting, and ultimately yield or quality of the plant and plant product. Diseases in plants are caused by sources as diverse as insects, fungi, molds, nematodes, and viruses. Counteractive measures to diseases have been implemented. The use of pesticides, insecticides, fungicides, hormone treatment, and other treatments are widely relied upon. These measures are not always effective or resistance to chemicals develops. Moreover, social acceptance of chemical treatments has waned over the years. Genetic breeding to confer resistance is an environmentally friendly alternative, but labor intensive and difficult to move resistance genes between species of plants. Other mechanisms to confer protection against plant diseases is desirable.

Various genes conferring protection for plants against diseases and insects have been identified. Many of these genes have been cloned as well. Introduction of these genes into plants and control of their expression is important for improving crop development and food production. In addition, transgenic resistance reduces the need for chemicals, which is beneficial for the environment and reduces labor and costs. For effective resistance, expression of the resistance genes in appropriate tissues is critical to their function. As such, tissue-specific promoters and accessory gene products that may increase expression are needed.

One organelle which is particularly important for the expression of genes in higher plant cells is the endoplasmic reticulum (ER). Briefly, the ER comprises the initial site of the protein secretory pathway, the site of the majority of fatty acid modification and triacylglycerol biosynthesis, and the site of an intracellular store of reversibly bound calcium, which is involved in various aspects of plant signal transduction. In developing seed storage tissue, the ER is the primary site of seed storage protein synthesis, folding and assembly. These processes require an array of chaperones, some of which (e.g., BiP, PDI, and GRP94) have been cloned. Calreticulin, which has been cloned as a cDNA from various animals and a few plants (e.g., barley (Chen et al., *Plant Cell* 6:835, 1994), Arabadopsis (Benedetti and Turner, *Plant Physiol.* 109:338, 1995), and corn (Napier et al., *J. Exp. Bot.* 46:1603, 1995)), is the primary calcium binding protein of the ER and may have a role in protein folding, assembly, and signal transduction. Calnexin is another calcium binding, chaperone protein in the ER, which has been cloned as a cDNA from various animals and from Arabidopsis.

The present invention discloses novel compositions for calreticulin and calnexin proteins, genomic sequences, and promoters, use of these proteins and sequences in controlling expression of resistance genes, and further, provides other related advantages.

SUMMARY OF THE INVENTION

Briefly stated, the present invention provides nucleic acid molecules which encode calreticulin and calnexin proteins, as well as promoter regions of the calreticulin and calnexin genes. More specifically, within one aspect of the present invention isolated nucleic acid molecules encoding calreticulin are provided, comprising a nucleic acid sequence that encodes SEQ ID NO:2, or a variant thereof. Within one embodiment, the sequence is SEQ ID NO:1.

Within other aspects of the present invention, isolated nucleic acid molecules are provided which encode calnexin, comprising a nucleic acid sequence that encodes SEQ ID NO:6, or a variant thereof. Within one embodiment, the sequence is SEQ ID NO:5.

Within other related aspects, isolated nucleic acid molecules are provided which encode soluble calnexin (e g., calnexin which lacks a transmembrane and C-terminal domain, as well as optionally, a signal peptide).

Also provided by the present invention are polypeptides encoded by the afore-mentioned nucleic acid sequences, vectors which comprise such sequences, and host cells which contains these vectors. Within one embodiment, the vector is an expression vector such as a binary *Agrobacterium tumefaciens* plasmid vector.

Within other aspects of the present invention, isolated nucleic acid molecules are provided, comprising a castor calreticulin promoter. Within one embodiment, such molecules comprise the nucleic acid sequence of SEQ ID NO:4, or a variant (including portions) thereof which has calreticulin-promoter activity.

Within yet other aspects, isolated nucleic acid molecules are provided, comprising a castor calnexin promoter. Within one embodiment, such molecules comprise the nucleic acid sequence of SEQ ID NO:8, or a variant (including portions) thereof which has calnexin-promoter activity.

Within other aspects, vectors are provided which contain one of the above-described calreticulin or calnexin promoters. Within a particularly preferred embodiment, such vectors further comprise a nucleic sequence encoding a foreign gene operably linked to said promoter. Representative examples of such foreign genes include genes which encode proteins, antisense genes and ribozyme genes. Within one embodiment the foreign gene confers resistance to a disease selected from the group consisting of Sclerotinia, sunflower head moth, canola flea beetle and soybean cyst nematode. Within other related aspects, host cells containing one of the above-described vectors are provided. Representative examples of suitable host cells include plant cells from soybean, canola, sunflower, or alfalfa.

Within further aspects of the invention, methods are provided for producing a foreign gene product, comprising the steps of (a) introducing a vector as described above into a host cell, wherein the vector contains a foreign gene in an expressible form, and (b) growing the host cell under conditions wherein the foreign gene is expressed. As noted above, representative examples of suitable host cells include plant cells such as those obtained from soybean, canola, sunflower, or alfalfa.

Within yet other aspects of the invention methods are provided for producing a plant which expresses a foreign gene, comprising the steps of (a) introducing a vector as described above into an embryogenic plant cell, wherein the vector contains a foreign gene in an expressible form, and (b) producing a plant from the embryogenic plant cell, wherein the plant expresses the foreign gene. Also provided are plants which can be made containing the nucleic acid molecules, or vectors, described herein.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS AND SEQUENCE LISTING

FIG. 1A–C presents the cDNA and translated protein sequence of castor calreticulin. Panel A shows the nucleic acid sequence of the cDNA. Panel B presents the predicted protein sequence of the longest open reading frame. Panel C is a hydrophobicity plot using the Kyte-Doolittle Algorithm (window size of 7 residues).

FIG. 2A–B shows that calstor calreticulin has a copy number of a single gene and that there is tissue-specific expression. Panel A is a Northern analysis of hybridization of calreticulin coding region to various plant tissues. Lane 1, endosperm 25 days after flowering; lane 2, 5 day germinated root; lane 3, 5 day germinated cotyledon; lane 4, 5 day germinated stem; lane 5, 5 day germinated endosperm; lane 6, greened cotyledon; lane 7, primary green leaf, lane 8, secondary leaf; lane 9, Arabadopsis leaf. Panel B is a Southern analysis after hybridization of calreticulin coding region to digested castor DNA. Lane 1, BamHI digest; lane 2, BglII digest; lane 3, HindIII digest. The number indicate the apparent lengths of the hybridizing fragments.

FIGS. 3A and 3B presents the genomic DNA sequence of calreticulin (SEQ ID NO:3) and the predicted amino acid sequence (SEQ ID NO:2). The TATA box is in bold face lettering and the putative polyadenylation signal is underlined. The transcriptional initiation site is indicated by underlined boldface lettering and is assigned nucleotide +1. The underlined amino acids denote the putative signal peptide; the double underlined amino acids denoted acidic amino acid/lysine rich domains. Asterisks indicate potential N-linked glycosylation sites. The translational stop codon is represented by three asterisks. The signature patterns for the calreticulin family of proteins are enclosed in parentheses.

FIG. 4A–B shows the structure of the calreticulin gene. Panel A is a schematic showing the genomic structure. Closed boxes denote translated regions, open boxes indicate introns, hatched boxes denote the 5' and 3' nontranslated regions of the gene. The TATA box, transcriptional start (ST), translational start (ATG), and poly A addition site are indicated by arrowheads. Sp, SphI; A, Age I; Bg, Bgl II; X, Xba I; P, Psi I; R, Eco RI; H, Hind III; Sc, Sca I; Sa, Sac I. Panel B is a schematic representation of the translated regions. Spaces denote splice sites. The line below maps the cDNA fragment that is used in Southern and Northern analyses.

FIG. 5 presents the nucleotide sequence of the castor calreticulin promoter region (SEQ ID. NO:4). "ST" is the transcriptional start site. Various consensus sequences for potential enhancer elements and transcription factors are labeled.

FIG. 6 is an autoradiogram showing the transcriptional start site determined by primer extension analysis using an primer complementary to nucleotides 72–92 of calreticulin cDNA. Lanes 1–4, DNA sequence of calreticulin genomic clone; lane 5, castor endosperm 3 day germinated mRNA; lane 6, castor endosperm 25 days after flowering mRNA; lanes 7–10, DNA sequence of M13 DNA.

FIGS. 7A–C contains graphs showing the concentration dependence of calcium binding for recombinant castor calreticulin. Panel A is a graph showing the binding of $^{45}$Ca to 0–10 $\mu$g of recombinant calreticulin in 1 mM $CaCl_2$. Panel B is a graph showing the binding of $^{45}$Ca to 0–10 $\mu$g of recombinant calreticulin in 2 $\mu$M $CaCl_2$. Panel C is a graph showing the binding of $^{45}$Ca to 3 $\mu$g of recombinant calreticulin in 0–10 mM $CaCl_2$. Closed circles, recombinant calreticulin; open circles, recombinant PDI; triangle, cytochrome C.

FIGS. 8A, 8B, and 8C are an SDS-PAGE analysis of the cellular location of castor calreticulin.

Figure 8A:
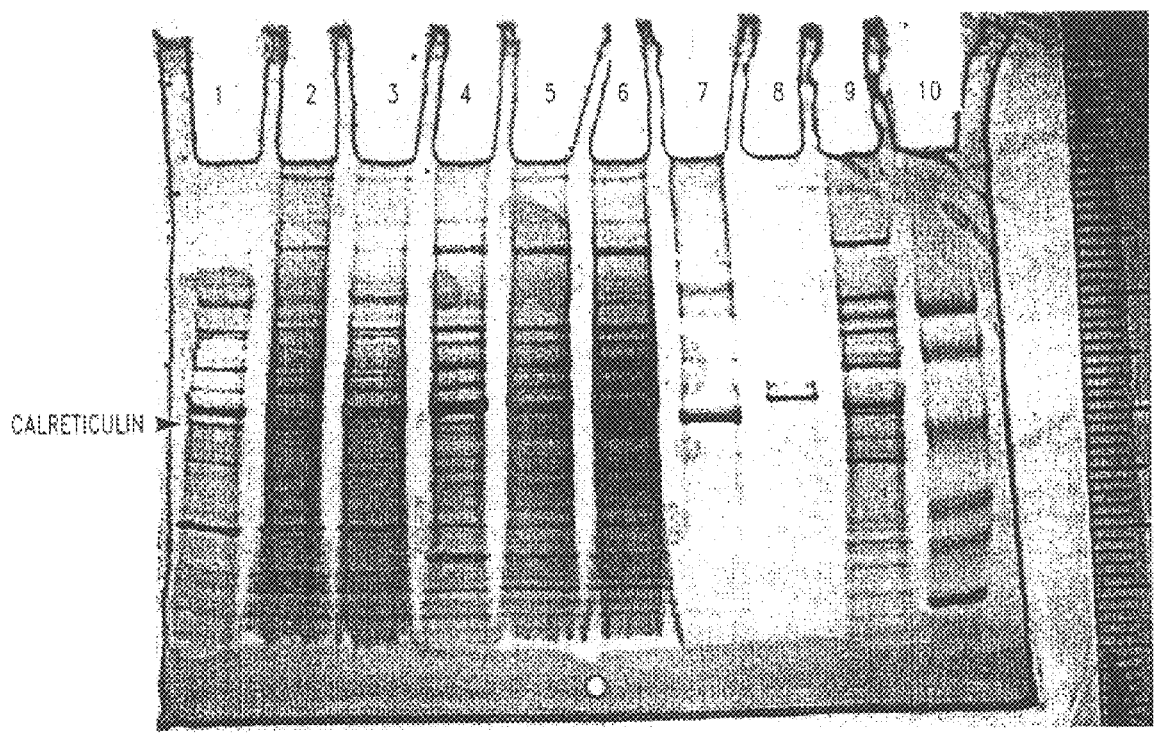
FIG. 8A is the Coomassie Blue stained gel.
Figure 8B:
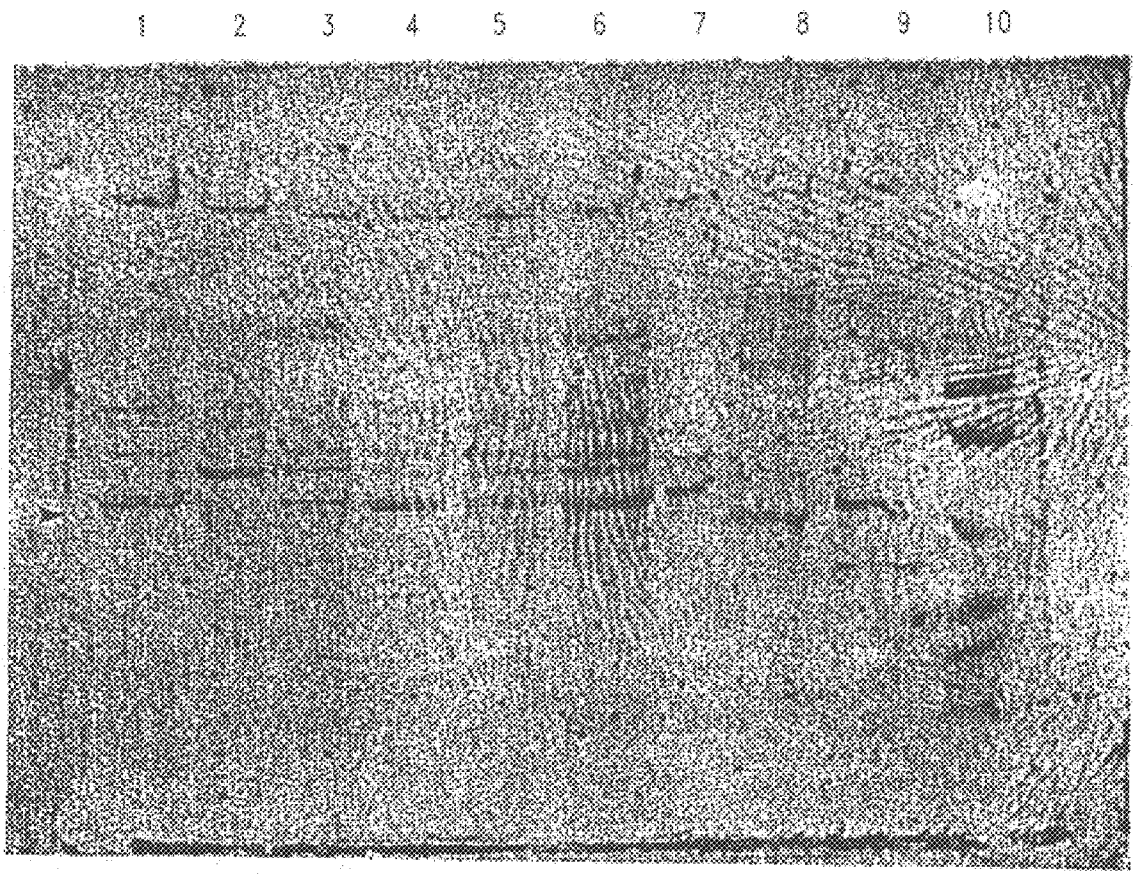
FIG. 8B is the gel after $^{45}$Ca overlay.
Figure 8C:
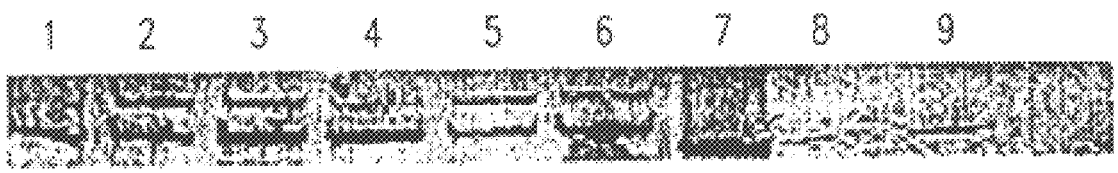

FIG. 8C is an immunoblot. Lane 1, 50 $\mu$g 0.1% Triton X-100 supernatant of castor ER (3 day germinated); lane 2, 50 $\mu$g of 0.1% Triton X-100 pellet of castor ER (3 day germinated); lane 3, 50 $\mu$g of 0.1% Triton X-100 total extract of castor ER (3 day germinated); lanes 4–6 are as lanes 1–3 except that the ER was prepared from developing castor seed endoplasm; lane 7, 5 $\mu$g recombinant calreticulin; lane 8, 5 $\mu$g recombinant PDI; lane 9, 5 $\mu$g recombinant calnexin; lane 10, prestained molecular weight markers.

Figure 9A:
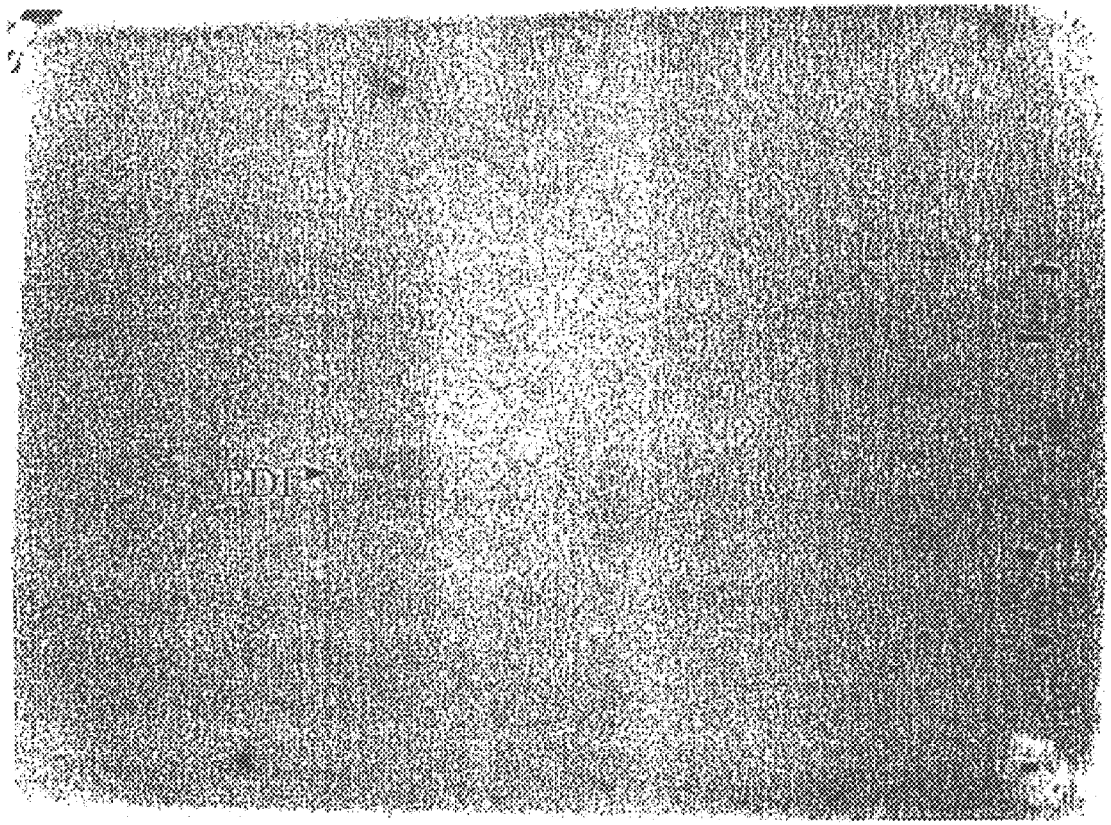

FIGS. 9A and 9B shows the binding of calreticulin to ER lumen proteins.

FIG. 9A is an autoradiogram showing $^{125}$I-calreticulin binding.

FIG. 9B is an SDS-PAGE analysis of calreticulin affinity column fractions. Lane 1, Triton X-100 solubilized ER membranes (10 $\mu$g protein); lanes 2–5, throughput and wash fractions; lane 6, 0.1 MKCL eluate; 5+; molecular weight markers; lane 7, 5 $\mu$g recombinant PDI. The gel was either silver stained (left side) to detect total protein or reacted with anti-PDI antisera (right side).

Figure 10A:
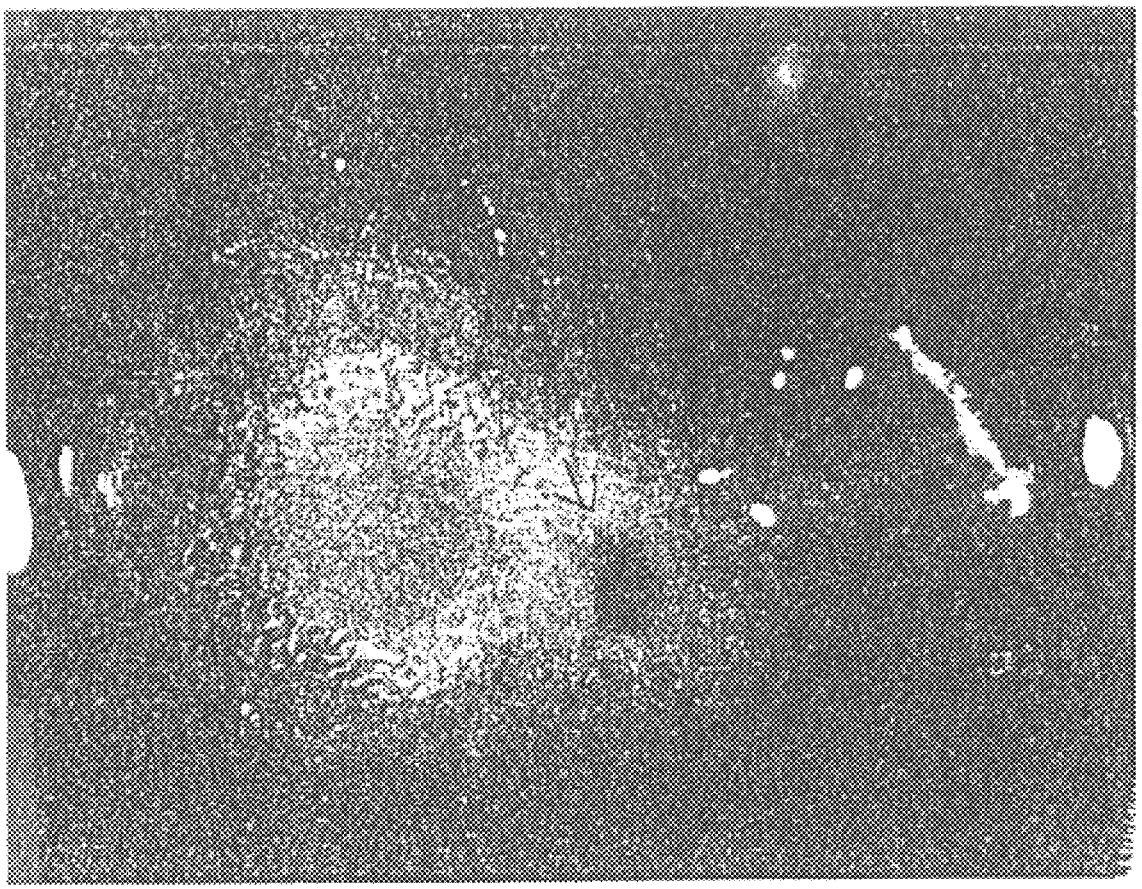
Figure 10B:
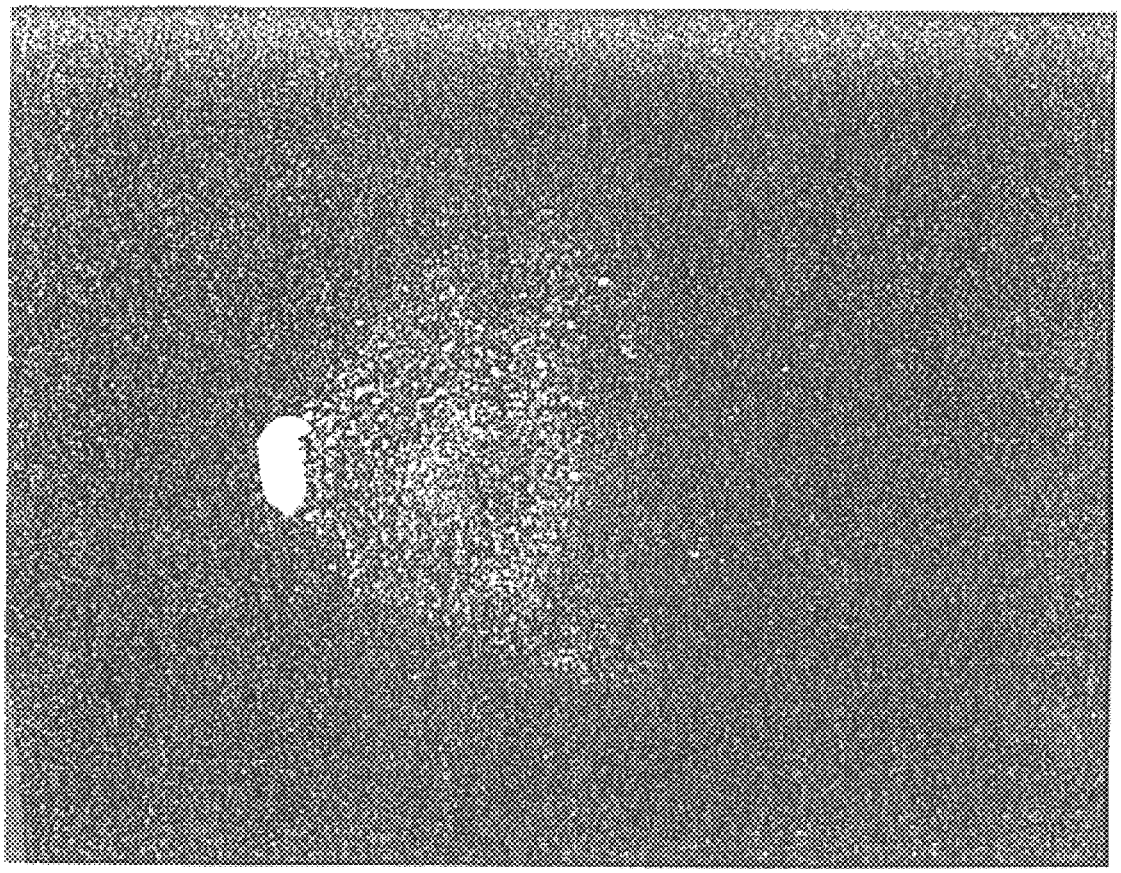
Figure 10C:
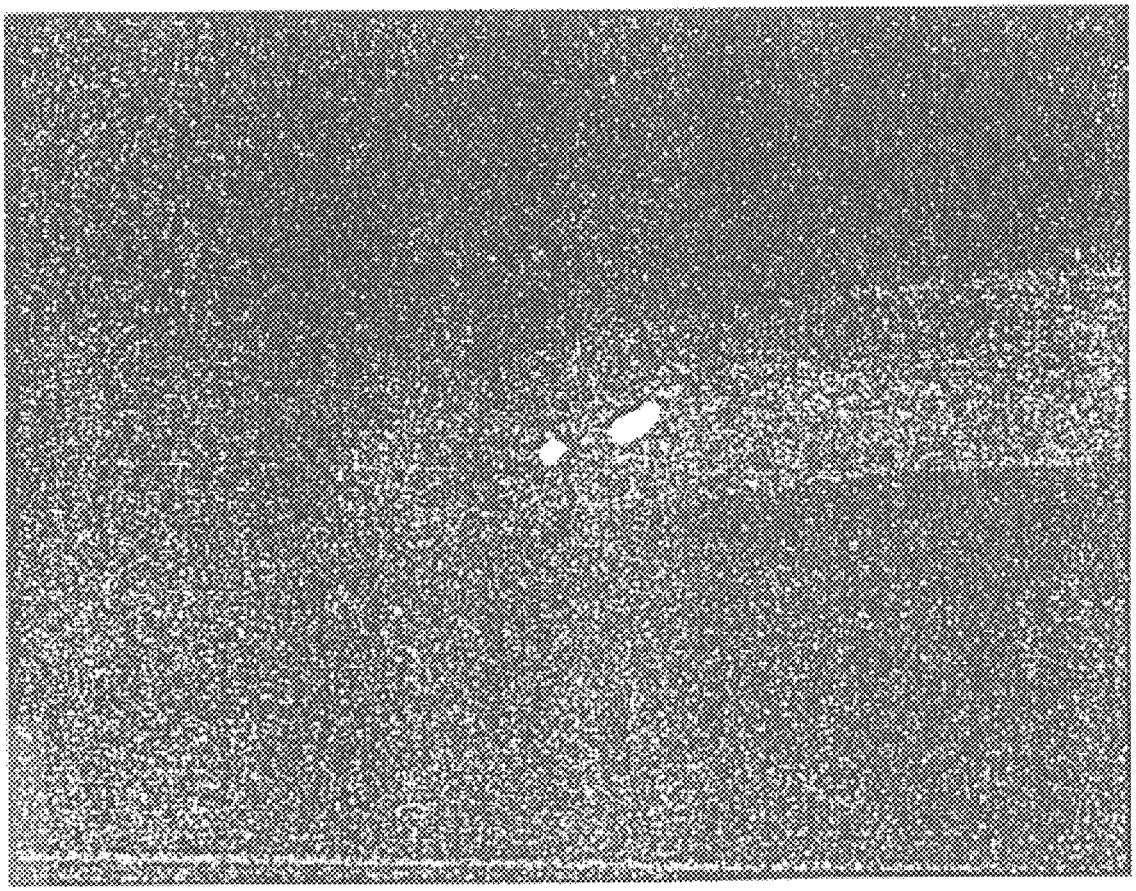

FIG. 10A–C shows tissue specific expression of β-glucuronidase in transgenic tobacco expressing a chimeric castor calreticulin promoter-GUS fusion. Panel A, vasculature; panel B, trichomes; panel C, root tip.

Figure 11:
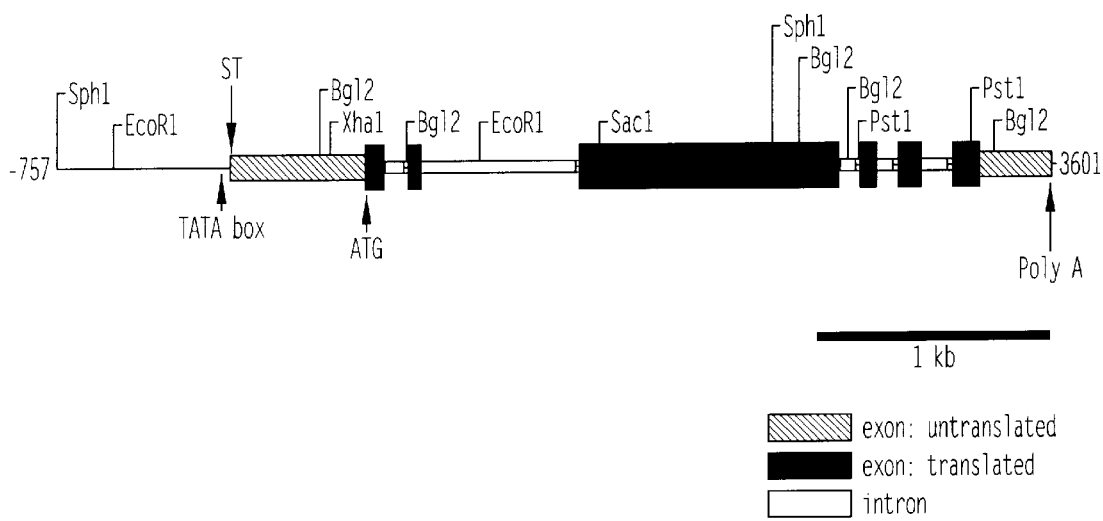

FIG. 11 is a schematic of the calnexin gene.

FIG. 12 is a DNA sequence of the castor calnexin promoter (SEQ ID NO:8). The potential TATA binding sites are underlined; the initiation methionine is bolded; the transcription start site is bolded at nucleotide +1.

Sequence ID Number 1 (SEQ ID NO:1) is a cDNA sequence of calreticulin.

Sequence ID Number 2 (SEQ ID NO:2) is a predicted calreticulin amino acid sequence.

Sequence ID Number 3 (SEQ ID NO:3) is a genomic sequence of calreticulin.

Sequence ID Number 4 (SEQ ID NO:4) is a promoter sequence of calreticulin.

Sequence ID Number 5 (SEQ ID NO:5) is a cDNA sequence of calnexin.

Sequence ID Number 6 (SEQ ID NO:6) is a predicted calnexin amino acid sequence.

Sequence ID Number 7 (SEQ ID NO:7) is a genomic sequence of calnexin.

Sequence ID Number 8 (SEQ ID NO:8) is a promoter sequence of calnexin.

Sequence ID Number 9 (SEQ ID NO:9) is a potential promoter element in the calnexin promoter sequence (SEQ ID NO:8).

Sequence ID Number 10 (SEQ ID NO:10) is a potential promoter element in the calnexin promoter sequence (SEQ ID NO:8).

Sequence ID Number 11 (SEQ ID NO:11) is a potential promoter element in the calnexin promoter sequence (SEQ ID NO:8).

Sequence ID Number 12 (SEQ ID NO:12) is a potential promoter element in the calnexin promoter sequence (SEQ ID NO:8).

Sequence ID Number 13 (SEQ ID NO:13) is a potential promoter element in the calnexin promoter sequence (SEQ ID NO:8).

Sequence ID Number 14 (SEQ ID NO:14) is a potential promoter element in the calnexin promoter sequence (SEQ ID NO:8).

Sequence ID Number 15 (SEQ ID NO:15) is a potential promoter element in the calnexin promoter sequence (SEQ ID NO:8).

Sequence ID Number 16 (SEQ ID NO:16) is a potential promoter element in the calnexin promoter sequence (SEQ ID NO:8).

DETAILED DESCRIPTION OF THE INVENTION

Prior to setting forth the invention, it may be helpful to an understanding thereof to set forth definitions of certain terms that will be used hereinafter.

As used herein, "calreticulin" refers to a polypeptide that binds calcium and is primarily resident in the endoplasmic reticulum. The amino acid sequence of one representative calreticulin from castor (*Ricinus communes L.*) has been deduced and is presented in SEQ ID NO:2. Within the context of this invention, it should be understood that calreticulin includes both the wild-type protein, as well as other variants (including alleles) of the native protein sequence. Briefly, such variants may result from natural polymorphisms or be synthesized by recombinant methodology, and differ from wild-type protein by one or more amino acid substitutions, insertions, deletions, or the like. Typically, amino acid substitutions are conservative. In the region of homology to the native sequence, variants should preferably have at least 90% amino acid sequence identity, and within certain embodiments, greater than 92%, 95%, or 97% identity. As will be appreciated by those skilled in the art, a nucleotide sequence encoding calreticulin or variant may vary from the native sequence presented in SEQ ID NO:1, due to codon degeneracies, nucleotide polymorphisms, or amino acid differences.

As used herein, "calnexin" refers to a polypeptide that binds calcium and is primarily resident in the endoplasmic reticulum. The amino acid sequence of one representative calnexin from castor (*Ricinus commnunis L.*) has been deduced and is presented in SEQ ID NO:6. Within the context of this invention, calnexin includes both the wild-type protein, as well as other variants of the native protein sequence. The nature of variants and the nucleotide sequence encoding calnexin, its alleles and variants is as discussed above for calreticulin. The nucleotide sequence encoding one representative native calnexin is presented in SEQ ID NO:5.

As used herein, a "promoter" refers to a nucleotide sequence that contains elements that direct the transcription of a linked gene. At minimum, a promoter contains an RNA polymerase binding site. More typically, in eukaryotes promoter sequences contain binding sites for other transcriptional factors that control the rate and timing of gene expression. Such sites include TATA box, CAAT box, POU box, AP1 binding site, and the like. Promoter regions may also contain enhancer elements.

An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleic acid analogues, or some combination of these.

A nucleotide molecule having "calreticulin promoter activity" refers to a promoter region containing elements responsive to factors that control calreticulin gene expression. In general, such a sequence promotes a similar expression pattern as for native calreticulin (e.g., tissue specificity, developmental timing). A sequence with calreticulin promoter activity may vary from the native sequence by base substitutions, insertions, and deletions, for example. Such alterations may affect the relative strength of the promoter, but should not affect the expression pattern. A nucleotide sequence having "calnexin promoter activity" is defined in similar fashion as for a sequence having caltreticulin promoter activity.

Calreticulin and Calnexin Genes and Gene Products

As noted above, the present invention provides compositions relating to calreticulin and calnexin genes, and methods for the use of the calreticulin and calreticulin gene products.

Isolation of Calreticulin and Calnexin Genes

The calreticulin and calnexin genes can be isolated from a wide variety of plants, such as the castor bean, given the disclosure provided herein. For example, within one embodiment, nucleic acid molecules which encode calreticulin or calnexin may be obtained from a cDNA or genomic expression library by screening with an antibody or antibodies reactive to calreticulin or calnexin (see, Examples herein; Sambrook, et al. *Molecular Cloning. A Laboratory Manual,* 2nd Ed., Cold Spring Harbor Laboratory Press, NY, 1987; Ausubel, et al. *Current Protocols in Molecular Biology,* Greene Publishing Associates and Wiley-Interscience, NY, 1987). Alternatively, using the sequence information provided herein, a probe sequence can be synthesized and labeled, such as with a radioactive label, enzymatic label, protein label, fluorescent label, or the like. The probe is then hybridized to a genomic library or a cDNA library in a phage, plasmid, phagemid, or other viral vector (see, for example, Sambrook et al., supra, Ausabel, et al., supra). DNA representing RNA or genomic nucleic acid sequence may also be obtained by amplification using sets of primers complementary to 5' and 3' sequences of the cDNA sequence, such as presented in SEQ ID NOS:1 and 5, or genomic sequences, such as presented in SEQ ID NOS:3 and 7.

cDNA sequence, genomic sequence, or portions of these sequences are preferably obtained by amplification. However, one skilled in the art will recognize that some procedures are more suitable for obtaining the desired sequence, depending on the sequence and its ultimate use. For example, the calreticulin and calnexin proteins are calcium binding proteins. Nucleic acid molecules which encompass this region (e.g., approximately amino acids 22 to 416 of SEQ ID NO:2) can be obtained by amplification using primer sequences derived from the 5' and 3' border region. For ease of cloning, restriction sites may also be incorporated into the primers.

Variants (including alleles) of the calreticulin or calnexin proteins provided herein may be readily isolated from natural variants (e.g., polymorphisms, mutants), synthesized or constructed. One skilled in the art recognizes that many methods have been developed for generating mutants (see, generally, Sambrook et al., supra; Ausubel, et al., supra).

Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, typically *E. coli*, but alternatively, other prokaryotes, yeast or other eukaryotes. Standard screening and vector growth protocols are used to identify mutant sequences and obtain high yields.

Similarly, deletions and/or insertions of the calreticulin and calnexin genes may be constructed by any of a variety of known methods. For example, the gene can be digested with restriction enzymes and religated such that sequence is deleted or religated with additional sequence such that an insertion or large substitution is made. Other means to generate variant sequences may be found, for example in Sambrook et al. (supra) and Ausubel et al. (supra). Verification of variant sequences is typically accomplished by restriction enzyme mapping, sequence analysis, or probe hybridization.

Vectors, Host Cells and Means of Expressing and Producing Protein

Calreticulin and calnexin may be expressed in a variety of host organisms. Preferably, these proteins are produced in bacteria, such as *E. coli*, for which many expression vectors have been developed and are available. Other host organisms suitable for production of calreticulin and calnexin include other bacteria, and eukaryotes, such as yeast (e.g., *Saccharomyces cerevisiae*), mammalian cells (e.g., CHO and COS-7), insect cells (e.g., Sf9) and plant cells.

A DNA sequence encoding calreticulin or calnexin is introduced into an expression vector appropriate for the host. Briefly, the calreticulin or calnexin sequence is derived from an existing cDNA or genomic clone or synthesized. A preferred means of synthesis is amplification of the gene from cDNA using a set of primers that flank the coding region or the desired portion of the protein. Restriction sites are typically incorporated into the primer sequences and are chosen with regard to the cloning site of the vector. If necessary, translational initiation and termination codons can be engineered into the primer sequences. The sequence encoding the protein is preferably codon-optimized for expression in the particular host. Thus, for example, if calreticulin is expressed in bacteria, the codons are optimized for bacterial usage. Codon optimization is accomplished by automated synthesis of the entire gene or gene region, ligation of multiple oligonucleotides, mutagenesis of the native sequence, or other techniques known to those in the art.

At minimum, the expression vector should preferably contain a promoter sequence. Other regulatory sequences however may also be included. Such sequences include an enhancer, transcription termination signal sequence, secretion signal sequence, origin of replication, selectable marker, and the like. The regulatory sequences are operationally associated with one another to allow transcription or translation.

The plasmids used herein for expression of calreticulin and calnexin include a promoter designed for expression of the proteins in a bacterial host. Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, RSV LTR, SV40, metallothionein promoter (see, e.g., U.S. Pat. No. 4,870,009) and other inducible promoters. For expression of the proteins, a promoter is inserted in operative linkage with the coding region for calreticulin or calnexin.

The vector may also contain a gene coding for a repressor protein, which is capable of repressing the transcription of an appropriate promoter that contains a repressor binding site. The promoter can be derepressed by altering the physiological conditions of the cell, for example, by the addition of a molecule that competitively binds the repressor, or by altering the temperature of the growth media. Preferred repressor proteins include, but are not limited to the *E. coli* lacI repressor responsive to IPTG induction, the temperature sensitive πcI857 repressor, and the like. The *E. coli* lacI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation. The transcription terminator may be obtained from the calreticulin or calnexin gene or from another gene, as long as it is functional in the host.

Within one embodiment, the vector is capable of replication in bacterial cells. Thus, the vector may contain a bacterial origin of replication. Preferred bacterial origins of replication include the f1-ori and col E1 origins of replication, especially the ori derived from pUC plasmids.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g., thymidine kinase (tk) in tk- hosts). However, drug markers are also available (e.g., G418 resistance and hygromycin resistance).

The sequence of nucleotides encoding calreticulin or calnexin may also include a sequence encoding a secretion signal, whereby the resulting peptide is a precursor protein processed and secureted. The resulting processed protein may be recovered from the periplasmic space or the fermentation medium. Secretion signals suitable for use are widely available and are well known in the art (von Heijne, *J. Mol. Biol.* 184:99–105, 1985). Prokaryotic and eukaryotic secretion signals that are functional in *E. coli* (or other host) may be employed. The presently preferred secretion signals include, but are not limited to, those encoded by the following *E. coli* genes: pelB (Lei et al.,*J. Bacteriol.* 169:4379, 1987), phoA, ompA, ompT, ompF, ompC, beta-lactamase, and alkaline phosphatase.). In addition, the signal sequence from the cek2 gene, which is functional in insect cells, may be employed. One of skill in the art can readily substitute secretion signals that are functional in yeast, insect or mammalian cells to secrete proteins from those cells.

Particularly preferred plasmids for expression of calreticulin and calnexin in *E. coli* include the pET expression vectors (see U.S Pat. No. 4,952,496; available from Novagen, Madison, Wis.). Such plasmids include pET3a, pET 11a, pET 12a–c, and pET 15b (Novagen, Madison, Wis.). Other plasmids suitable for use in the present invention include the pKK plasmids, particularly pKK 223-3, which contains the tac promoter, (Pharmacia, Uppsala, Sweden; see also Brosius et al., *Proc. Natl. Acad. Sci.* 81:6929, 1984; Ausubel et al., *Current Protocols in Molecular Biology;* U.S. Pat. Nos. 5,122,463, 5,173,403, 5,187,153, 5,204, 254, 5,212,058, 5,212,286, 5,215,907, 5,220,013, 5,223,483, and 5,229,279). Other plasmids include the pIN-IIIompA plasmids (see U.S. Pat. No. 4,575,013; see also Duffaud et al., *Meth. Enz.* 153:492–507, 1987), such as pIN-IIIompA2. One skilled in the art will appreciate that there are a wide variety of suitable vectors for expression in bacterial cells and which are readily obtainable.

Baculovirus vectors, such as pBlueBac (also called pJVETL and derivatives thereof), particularly pBlueBac III, (see, e.g., U.S. Pat. Nos. 5,278,050, 5,244,805, 5,243,041, 5,242,687, 5,266,317, 4,745,051, and 5,169,784; available from Invitrogen, San Diego) may also be used for expression of the polypeptides in insect cells. A DNA construct may be made in baculovirus vector pBluebac III and then co-transfected with wild type virus into insect cells *Spodoptera frugiperda* (sf9 cells; see, e.g., Luckow et al., *Bio/technology* 6:47–55, 1988, and U.S. Pat. No. 4,745, 051).

Preferred bacterial hosts for the expression vectors contain chromosomal copies of DNA encoding T7 RNA polymerase operably linked to an inducible promoter, such as the lacUV promoter (see U.S. Pat. No. 4,952,496). Such hosts include, but are not limited to, lysogens *E. coli* strains HMS174(DE3)pLysS, BL2 1 (DE3)pLysS, HMS174(DE3) and BL21 (DE3).

Protein is isolated by standard techniques, such as affinity, chromatography, size exclusion chromatography, ionic exchange chromatography, HPLC and the like. An isolated protein should show a single band by Coomassie blue stain of SDS-PAGE.

Assays for Protein Function

Calreticulin and calnexin proteins are both calcium-binding proteins. In addition, these proteins are found mainly in the endoplasmic reticulum and likely function as chaperones and are involved in protein stabilization and folding. Within the context of this invention, chaperone activity is desired and calcium binding activity may be important as well. Thus, variants of calreticulin or calnexin may be assayed for each of these two activities by well-known assay methods.

Chaperone activity is evidenced by the ability of calnexin and calreticulin to bind in vitro to $Glc_1Man_9GlcNAc_2$ oligosaccharide (Ware et al., *J. Biol. Chem.* 270: 4697–4704, 1995; Vassilakos et al., *Molecular Chaperones & the Heat Shock Response,* Cold Spring Harbor Laboratory Press, NY, 1996). Briefly, recombinant soluble calnexin (e.g., residues 27–470 of Sequence ID No. 6) or calreticulin are incubated with tritiated mannan (e.g., $Glc_1Man_9GlcNAc_2$ oligosaccharide) and the complex is bound to a nickel-agarose affinity column. The column is washed with binding buffer to remove unbound mannan, and bound mannan is specifically eluted with 0.1 M methyl mannopyranoside (see, Ware et al., supra). Additional assays that are optionally performed are the enhancement of the assembly of class I heavy chains with β2-microglobulin or assembly of other proteins and prevention of the interaction of calnexin with class I heavy chains with the oligosaccharide processing inhibitor castanospermine (Vassilakos et al., *EMBO J.* 15: 1495–1506, 1996).

Calcium binding activity is conveniently measured in the following assay. Briefly, purified calreticulin or calnexin, preferably recombinant protein, is spotted and dried onto nitrocellulose membrane. Generally, approximately 1–10 μg of protein is used. The dot blots are incubated in Tris buffer containing KCl, $CaCl_2$, and $[^{45}Ca]Cl_2$ for 10–20 min at room temperature with rotation. The dot blots are washed in the same buffer without $[^{45}Ca]Cl_2$ and counted by a liquid scintillation counter.

The alleles and variants described herein, including substitutions, insertions and deletions, are useful with the context of this invention, as long as chaperone activity is present as at least 10% of wild-type activity. When calcium binding activity is desired, the alleles and variants described herein should have at least 10% of wild-type activity.

Promoter Regions of Calreticulin and Calnexin Genes

As described above, this invention provides promoters of calreticulin and calnexin genes and uses of the promoters in controlling foreign gene expression.

Briefly, the promoter regions of calreticulin (SEQ ID NO:4) and calnexin genes (SEQ ID NO:8) were initially identified in genomic clones by classical consensus promoter sequences located upstream of the coding region. Such sequences include TATA and CAAT sequences. In addition, there are two putative wound inducible factor sequences at positions –830 and –1086 (nucleotides 1005, 757 in SEQ ID NO:4) of calreticulin promoter. Verification of promoter activity for the calreticulin promoter was assessed by cloning the upstream sequence into a plasmid containing a reporter gene. Briefly, a 1.8 kb SphI/XbaI DNA fragment was inserted into pBI121 (Jefferson et al., *EMBO J.* 6: 3901–3907, 1987) in place of the CaMV 35S promoter. If a promoter is present, transcription of the GUS reporter gene will ensue. This construct, called calpro/pBI 121, was used to transform tobacco leaf discs via *Agrobacterium tumefaciens*-mediated transformation. GUS (β-glucuronidase) activity was detected in tissue sections of transformed plants by colorometric assay using the substrate 5-bromo-4-chloro-3-indoyl-glucuronide sodium salt. By assaying different plant tissues, a pattern of expression is established. The calreticulin promoter has been shown herein to be preferentially expressed in floral regions of the plant, including developing and germinating seed and the vasculature. Photosynthetic tissues, especially mature leaves, lack detectable promoter activity.

This method may be generalized to assay promoter activity of any DNA fragment by constructing a vector containing the DNA fragment upstream of a suitable reporter gene. Reporter genes include, but are not limited to, GUS, luciferase, β-galactosidase, and green fluorescent protein. Examples of suitable constructs are discussed below.

An alternative assay for promoter activity is a transient expression assay. In such a method, a construct containing the candidate promoter region is placed upstream of a reporter gene (e.g., GUS, luciferase, β-galactosidase, green fluorescent protein) and transfected into plant cells by bombardment (see, *GUS Protocols. Using the GUS gene as a reporter of gene expression,* Sean Gallagher (ed.), Academic Press, Inc., 1992). Reporter activity is measured approximately a few hours later. When using this method, the plasmid or DNA may be an Agrobacterium-based plasmid, pUC-based plasmid, or other vector. Various plant tissues may be used, which will provide some information regarding cell-specificity of the promoter. Approximately 100 mg of tissue is needed for bombardment.

Minimal promoter sequences and variant promoter sequences are constructed by standard techniques, such as deletion by restriction digestion and oligonucleotide-mediated mutagenesis. By making progressively larger deletions from the 5' end of the initial fragment containing a promoter and assaying for promoter activity, the minimal promoter region is determined.

Foreign Genes

As discussed above, this invention provides vectors for the expression of foreign or heterologous genes under control of the calreticulin or calnexin promoter sequence. Within the context of this invention, a foreign gene is any gene sequence other calreticulin or calnexin, including for example, other proteins, antisense sequences, or ribozyme sequences.

Preferred foreign genes encode insect and disease resistance gene products or seed storage proteins. Insect and disease resistance genes are well known. Some of these genes are present in the genome of plants and have been genetically identified. Others of these genes have been found in bacteria.

Particularly well-known insect resistance genes are the crystal genes of *Bacillus thuringiensis*. The crystal genes are active against various insects, such as lepidopterans, Diptera, and mosquitoes. Many of these genes have been cloned. For examples, see GenBank Accession Nos. X96682, X96684; M76442, M90843, M89794, M22472, M37207, D17518, L32019, M97880, L32020, M64478, M11250, M13201, D00117, M73319, X17123, X86j902, X06711, X13535, X54939, X54159, X13233, X54160, X56144, X58534, X59797, X75019, X62821, Z46442, U07642, U35780, U43605, U43606, U10985; Kostichka et al., *J. Bacteriol.* 178: 2141, 1996; U.S. Pat. No. 5,317,096, U.S. Pat. No. 5,254,799; U.S. Pat. No. 5,460,963, U.S. Pat. No. 5,308,760, U.S. Pat. No. 5,466,597, U.S. Pat. No. 5,2187,091, U.S. Pat. No. 5,382,429, U.S. Pat. No. 5,164, 180, U.S. Pat. No. 5,206,166, U.S. Pat. No. 5,407,825, U.S. Pat. No. 4,918,066; PCT Applications WO 95/30753, WO 94/24264; AU 9062083; EP 408403 B1, EP 142924 B1, EP 256,553 B1, EP 192,741 B1; JP 62-5693;. Gene sequences for these proteins may be obtained by standard and routine technologies, such as probe hybridization of a *B. thuringiensis* library or amplification (see generally, Sambrook et al., supra, Ausubel et al., supra). The probes and primers may be synthesized based on publicly available sequence information.

Other resistance genes to Sclerotinia, sunflower head moth, canola flea beetle, soybean cyst nematode, tobacco mosaic virus, flax rust, rice blast, powdery mildew, verticillum wilt, crown rust, potato beetle, aphid, other fungal and bacterial infections, may be obtained and are useful within the context of this invention. Examples of insect and disease resistance genes may be found in the following: genes for lytic peptides that combat bacterial infections (WO 96/03522); rust disease resistance gene from flax plants (WO 95/29238); gene encoding Rps2 protein from *Arabidopsis thaliana* that confers disease resistance to pathogens carrying the avrRpt2 avirulence gene (WO 95/28478); gene encoding antimicrobial protein of about 3 kD from seeds of Aralia or Impatiens (WO 95/24486); gene encoding a lectin-like protein of kidney bean confers insect resistance (JP 71-32092); Hm1 disease resistance gene to *C. carbonum* from maize (WO 95/07989); protein kinase gene (Pto) whose product confers disease resistance on plants responding to an avirulence gene in plant pathogens (WO 95/05731); gene for antimicrobial protein from Allium with antifungal and antibacterial properties (WO 95/05743); gene for insect resistance (U.S. Pat. No. 5,496,732; U.S. Pat. No. 5,349,126); genes for fungal resistance (EP 616035); genes for pathogen resistance (EP 392225); ribonuclease gene for conferring resistance to pathogenic fungi and nematodes (WO 94/18335); soybean beta-1,3-endo-glucanase gene for conferring resistance to various fungi (JP 43-20631); genes for Bandeiraea II lectin and chymopapain for conferring resistance to fungi, including Sclerotina, Aspergillus and Fusarium (EP 502719); genes encoding animal-derived antimicrobial peptides, such as mahainin or defensin (WO 90/11770); gene encoding arcelin seed storage protein that conveys insect resistance, especially to bean bruchid pests (U.S. Pat. No. 5,270,200); trypsin inhibitor gene that confers insect resistance (U.S. Pat. Nos. 5,218,104 and 5,306,863). In addition, general methods for identification and isolation of plant disease resistance genes are disclosed (WO 95/28423). Any of these gene sequences suitable for insertion in a vector according to the present invention may be obtained by standard recombinant technology techniques, such as probe hybridization or amplification. When amplification is performed, restriction sites suitable for cloning are preferably inserted.

Vectors, Host Cells, and Methods for Transformation

As noted above, the present invention provides vectors capable of expressing calreticulin, calnexin or other genes under the control of the calreticulin or calnexin promoter. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed above and, for example, in Sambrook et al. (supra) and in Ausubel et al. (supra).

Vectors that are functional in plants are preferably binary plasmids derived from Agrobacterium plasmids. Such vectors are capable of transforming plant cells. These vectors contain left and right border sequences that are required for integration into the host (plant) chromosome. At minimum, between these border sequences is the gene to be expressed under control of a promoter. In preferred embodiments, a selectable marker and a reporter gene are also included. For ease of obtaining sufficient quantities of vector, a bacterial origin that allows replication in *E. coli* is preferred.

As discussed above, this invention provides the expression in plants of a foreign gene under control of the calreticulin or calnexin promoter. The choice of the foreign gene depends in part upon the desired result. For example, when disease or insect resistance to a pest or pathogen, a preferred gene is specific to the disease or insect.

In certain preferred embodiments, the vector contains a reporter gene and calreticulin or calnexin. The reporter gene should allow ready determination of transformation and expression. The GUS (β-glucoronidase) gene is preferred (U.S. Pat. No. 5,268,463). Other reporter genes, such as β-galactosidase, luciferase, GFP, and the like, are also suitable in the context of this invention. Methods and substrates for assaying expression of each of these genes are well known in the art. The reporter gene should be under control of a promoter that is functional in plants. Such promoters include CaMV 35S promoter, mannopine synthase promoter, ubiquitin promoter and DNA J promoter. Co-expression of calreticulin or the globular domain of calnexin with the foreign gene may enhance expression of the foreign gene by increased chaperone activity.

The vector should contain a promoter sequence. Preferably, for expression of a foreign gene, the promoter is a calreticulin promoter or a calnexin promoter. The sequence of the calreticulin promoter region is presented in SEQ ID NO:4, and the sequence of the calnexin promoter region is presented in SEQ ID NO:8. The entire promoter region does not need to be in the vector. However, the vector should contain at least the minimum sequence to promote transcription of the associated gene. Delineation of the minimum sequence is discussed above. In general, a minimum promoter region is about 200 bases upstream of the transcription start site, but may be as long as 300–500 bases. As well, variants of the promoter region may be used as long as at least 1% of native promoter activity is retained, and more preferably, greater than 10%, 20%, or 50% of native promoter activity. As provided herein, variants may be the result of natural polymorphisms, or synthesized mutants. Variants may also be derived from highly related promoter sequences, such as calreticulin promoter sequences from other plants, isolated by hybridization as described herein.

Preferably, the vector contains a selectable marker for identifying transformants. The selectable marker may confer a growth advantage under appropriate conditions. Generally, selectable markers are drug resistance genes, such as neomycin phosphotransferase. Other drug resistance genes are known to those in the art and may be readily substituted. The selectable marker has a linked constitutive or inducible promoter and a termination sequence, including a polyadenylation signal sequence.

Additionally, a bacterial origin of replication and a selectable marker for bacteria are preferably included in the vector. Of the various origins (e.g., colEI, fd phage), a colEI origin of replication is preferred. Most preferred is the origin from the pUC plasmids, which allow high copy number.

A general vector suitable for use in the present invention is based on pBI121 (U.S. Pat. No. 5,432,081) a derivative of pBIN19. Other vectors have been described (U.S. Pat. No. 4,536,475) or may be constructed based on the guidelines presented herein. The plasmid pBI121 contains a left and right border sequence for integration into a plant host chromosome. These border sequences flank two genes. One is a kanamycin resistance gene (neomycin phosphotransferase) driven by a nopaline synthase promoter and using a nopaline synthase polyadenylation site. The second is the *E. coli* GUS gene under control of the CaMV 35S promoter and polyadenylated using a nopaline syntase polyadenylation site. The CaMV 35S promoter is excised by appropriate restriction. For example, a Hind III/BamH I double digestion will liberate the CaMV promoter sequence. The promoter may also be liberated by a partial Sph I/ complete Xba I digestion. The calreticulin or calnexin promoter is inserted in its place. Either the promoter sequence is amplified, synthesized, or isolated from a clone with compatible restriction sites or sites are added by standard methodologies, such as the addition of adaptors or linkers. Plasmid pBI121 also contains a bacterial origin of replication and selectable marker.

In certain embodiments, the vector may contain a calreticulin or calnexin gene under control of a promoter. The promoter may be the calreticulin or calnexin promoter or a strong, constitutive promoter, such as CaMV 35S promoter. Other elements that are preferred for optimal expression (e.g., transcription termination site, enhancer, splice site) may also be included. The calreticulin gene is preferably full-length; the calnexin gene preferably encodes only the globular domain and does not contain the transmembrane domain. When less than the full-length calreticulin or calnexin gene is used, it is important to retain the chaperone activity. The genes may alternatively be expressed as fusion proteins with a reporter gene, for example. The co-expression of calreticulin or calnexin may serve to enhance expression of the foreign gene.

Plant Transformation Methods

As discussed above the present invention also provides methods for producing a plant which expresses a foreign gene, comprising the steps of (a) introducing a vector as described above into an embryogenic plant cell, wherein the vector contains a foreign gene in an expressible form, and (b) producing a plant from the embryogenic plant cell, wherein the plant expresses the foreign gene.

Vectors may be introduced into plant cells by any of several methods. For example, DNA may be introduced as a plasmid by Agrobacterium in co-cultivation or bombardment. Other transformation methods include electroporation, $CaPO_4$-mediated transfection, and the like. Preferably, DNA is first transfected into Agrobacterium and subsequently introduced into plant cells. Most preferably, the infection is achieved by co-cultivation. In part, the choice of transformation methods depends upon the plant to be transformed. For example, monocots generally cannot be transformed by Agrobacterium. Thus, Agrobacterium transformation by co-cultivation is most appropriate for dicots and for mitotically active tissue. Non-mitotic dicot tissues can be efficiently infected by Agrobacterium when a projectile or bombardment method is utilized. Projectile methods are also generally used for transforming sunflowers and soybean. Bombardment is used when naked DNA, typically Agrobacterium or pUC-based plasmids, is used for transformation or transient expression.

Briefly, co-cultivation is performed by first transforming Agrobacterium by freeze-thawing (Holsters et al., *Mol. Gen. Genet.* 163: 181–187, 1978) or by other suitable methods (see, Ausubel, et al., supra; Sambrook et al., supra). Agrobacterium containing the plasmid are grown overnight at 28° C. with continuous agitation in YEP medium in the presence of kanamycin (when the selectable marker is $kan^R$) or colony selected and purified on agar-containing medium. An aliquot or colony is grown to mid-log phase (e.g., OD=0,5) in medium containing 12.5 mM MES, 1 g/L NH4Cl and 0.3 g/L MgSO4 at pH 5.7. Approximately $10^9$ cells/ml Agrobacterium is incubated with sterile leaf disks, protoplasts or meristematic tissue for 1 hr. The discs are then washed in sterile distilled water and cultivated on standard plant tissue culture medium containing kanamycin.

For microprojectile bombardment, seeds are surface sterilized in 20% bleach solution with two drops of Tween 20 per 50 ml for 30 min and rinsed twice with distilled water. Seeds are then imbibed in distilled water for 60 min, and the cotyledons are broken off to produce a clean fracture at the plane of the embryonic axis. The explants are then bisected longitudinally between the primordial leaves. The explants are placed cut surface up on GBA medium with mineral and vitamin additives, sucrose, indole-3-acetic acid, gibberellic acid and phytagar. Thirty to forty explants are placed in a circle at the center of a 60 mm plate and bombarded with approximately 4.7 mg of 1.8 $\mu$m tungsten microprojectiles' in 1.5 $\mu$l aliquots by a PDS 1000® particle acceleration device. Each plate is bombarded twice through a 150 $\mu$m Nytex screen placed about 2 cm above the samples. Freshly bombarded explants are placed in a suspension of transformed Agrobacterium for 30 min and then transferred to GBA medium with the cut surfaces down for 3 days with an 18 hr light cycle. Explants are transferred to medium lacking growth regulators but containing drug for selection and grown for 2–5 weeks. After 1–2 weeks more without drug selection leaf samples from green, kanamycin-resistant shoots are assayed for the presence of neophosphotransferase activity. Positive shoots may be grafted to in vitro grown rootstock and transferred to soil.

Within one embodiment of the invention, a genomic DNA sequence containing the calreticulin promoter region is placed upstream from the *E coli* β-glucuronidase gene in the plasmid pBI121 (Jefferson et al., *EMBO J.* 6:3901–3907, 1987). The CaMV 35S promoter in this plasmid is removed and replaced with a fragment that contains the 5' flanking region of castor calreticulin gene. This construct is used to transform tobacco leaf discs via *Agrobacterium tumefaciens*-mediated transformation as described herein. Histochemical analysis of tissue sections is performed by adding the substrate 5-bromo-4-chloro-3-indoyl-glucuronide sodium salt in buffer containing potassium ferrocyanide. Plant tissue is incubated in this mixture at 37° C. overnight and β-glucuronidase activity is determined calorimetrically (Jefferson, *Plant Molecular Biology Reporter* 5:387–405, 1987). Tissues of transgenic tobacco exhibit strong GUS activity in the floral regions of the plant, including developing and germinating seeds and the vasculature. Photosynthetic tissues, especially mature leaves, lack measurable GUS activity.

The following examples are offered by way of illustration, and not by way of limitation.

EXAMPLES

Example 1

Cloning of the Gene for *Ricinus communis L.* Calreticulin

Castor seed (*Ricinus communis L.* var. Hale) is obtained from R.T. Bothwell Seed Company (Plainview, Tex.). Plants are grown in the greenhouse in soil (supplementary light 400μ einsteins m-1 s-1, 14 h photoperiod) at 25° C. for light periods and 20° C. for dark periods. Germinating seeds are prepared by surface sterilization (5% by volume bleach) for 10 minutes, followed by soaking in running tap water overnight. The seeds are sown in moist vermiculite and germinated in the dark at 30° C. for between 3–5 days. Plant tissues are excised, rinsed in ice cold distilled water, briefly dried, fast frozen in liquid nitrogen and may be stored at −80° C.

Total RNA is isolated using the phenol/SDS procedure of Martin and Northcote (*Planta* 151:189–197, 1981). Poly (A)+RNA is isolated from total RNA using oligo dT-Sepharose spin columns (Pharmacia, Piscataway, N.J.). Messenger RNA (5 μg mRNA) from 3d germinated castor endosperm is used as template for cDNA synthesis using the Lambda ZAP cDNA synthesis kit (Stratagene, La Jolla, Calif.). Size selected cDNA is ligated to the Uni-ZAP XR vector (Stratagene) and then packaged with the Gigapack Gold (Stratagene) in vitro lambda packaging system. Purified castor seed endosperm endoplasmic reticulum (ER) and rabbit polyclonal antisera to castor reticuloplasmin are prepared according to published methods. (Coughlan et al., *Eur. J Biochem.* 275:215–224, 1996).

The expressed cDNA library is immune screened with antisera specific for plant ER reticuloplasmins by standard methods (Sambrook et al., *Molecular Cloning: A Laboratory Manual*, 2nd Edition, Cold Spring Harbor Laboratory Press, 1989). Positively reacting plaques from an immune screen of $2 \times 10^5$ recombinant plaques are purified to homogeneity by repeated screening, the cDNA inserts excised in Bluescript SK, and the DNA sequence of both strands are determined by the dideoxynucleotide chain-termination method (Sanger et al., *Proc. Natl. Acad Sci. USA* 74:5463–5467, 1977) using the T7 polymerase kit (United States Biochemical, Cleveland, Ohio). Northern and Southern blot analysis of isolated RNA and DNA is performed as in Sambrook et al. (supra). Primer extension analysis to map the transcription start site is carried out as in Calzone et al. (*Methods in Enzymology* 152:611–632, 1987).

The availability of antisera specific for plant ER reticuloplasmins (Coughlan et al., *Eur. J. Biochem.* 275:215–224, 1996) allows cloning all of the ER lumen abundant proteins in a non-biased manner by screening an 3d germinated castor bean endosperm expression cDNA library in Lambda ZAP for immune positive plaques. Among the immune positive clones obtained is one designated pC1, which contained a 1.5 kb cDNA insert (SEQ ID NO:1). Translation of the full sequence predicts a 6 nt 5' untranslated region followed by a 1245 nt open reading frame from nt 7-1251 encoding a putative protein of 415 residues (SEQ ID NOS:1 and 2) followed by a 250 nt 3' untranslated with a consensus polyadenylation signal (TATAAT) 31 nt from the polyA sequence. A comparison of the deduced protein sequence to the EMBL or GenBank databases showed a strong homology to the endoplasmic reticulum resident soluble calcium binding protein calreticulin (87% identity, 93% similarity to tobacco calreticulin (Denecke et al., *Plant Cell* 7:391–406, 1995) and 76–%78% identity, 87%–88% similarity (i.e., same class of amino acid, such as acidic, basic, hydrophobic, neutral, hydrophilic) to barley and maize calreticulin (Chen et al., *Plant Cell* 6:835–843, 1994; Napier et al., *J. Exp. Bot.* 46:1603–1613, 1995), 57% identity, 73% similarity to rabbit calreticulin (Fliegel et al., *J. Biol. Chem.* 264:21522–21528, 1989).

Castor genomic DNA from 5d germinated cotyledons is isolated as described (Dellaporta et al., *Plant Mol. Biol. Rep.* 1:19–22, 1983), partially digested by Sau3A I, fractionated by agarose gel electrophoresis, and treated with calf intestine alkaline phosphatase. Prepared castor genomic DNA is ligated to predigested Lambda EMBL 3/BamHI (Stratagene, La Jolla, Calif.), which is then packaged with Gigapack Gold II (Stratagene) packaging extract and infected into *E. coli* strain LE392 as host. Approximately $1 \times 10^6$ independent recombinants are obtained. The library is amplified once to obtain a final library titer of $1.4 \times 10^9$ pfu/ml.

About $8 \times 10^5$ pfu from a Lambda EMBL 3 library of castor genomic DNA is screened at normal stringency with the calreticulin cDNA clone which had been $^{32}$P-labelled to high specific activity using a random hexamer priming kit (Pharmacia, Piscataway, N.J.) using ($\alpha^{32}$P)dCTP (Amersham, Arlington Hts., Ill.) and DNA polymerase I (Klenow fragment) (Boehringer Mannheim, Indianapolis, Ind.). Duplicate plaque lifts are performed, and the bound DNA is denatured as in Sambrook et al. (supra). The nylon filters are prehybridized for one hour at 42° C., in 50% (v/v) formamide, 6× SSC (0.9M NaCl, 90 mM sodium citrate pH 7.0), 0.5% (w/w) SDS, 5× Denhardts, 100 μg/ml salmon sperm DNA and then hybridized to radiolabeled probe in the same solution without Denhardts for 16 hours at 42° C. The filters are washed twice with 0.2× SSC, 0.5% (w/v) SDS at 42° C. for one hour. Filters are exposed to Kodak X-OMAT-AR film between intensifying screens at −80° C. Signals present on duplicate filters are picked and subjected to rescreening. Positively reacting plaques are purified to apparent homogeneity.

Phage DNA is isolated according to Sambrook et al. (supra). The genomic inserts are released from the Lambda arms by SalI digestion, purified using a Band Prep kit (Pharmacia, Piscataway, N.J.), and ligated into the SalI cloning site of the plasmid Bluescript SK II+ (Stratagene, La Jolla, Calif.). Ligation products are transformed into *E. coli* DH5α. Putative transformed plasmids are verified by restriction analysis of miniprep DNA (Sambrook et al., supra). Both strands of the entire insert are sequenced by the dideoxy chain termination method (Sanger et al., *Proc. Natl. Acad. Sci. USA* 74:5463–5467, 1977), using a primer walking strategy with a Taq dideoxy terminator cycle sequencing kit (Applied Biosystems, Foster City, Calif.). The products are separated electrophoretically and the data processed by a Perkin-Elmer ABI 377 automated sequencer. DNA sequences are complied and analyzed using both Macvector/ DNA and the GCG/Wisconsin package.

Figure 1C:
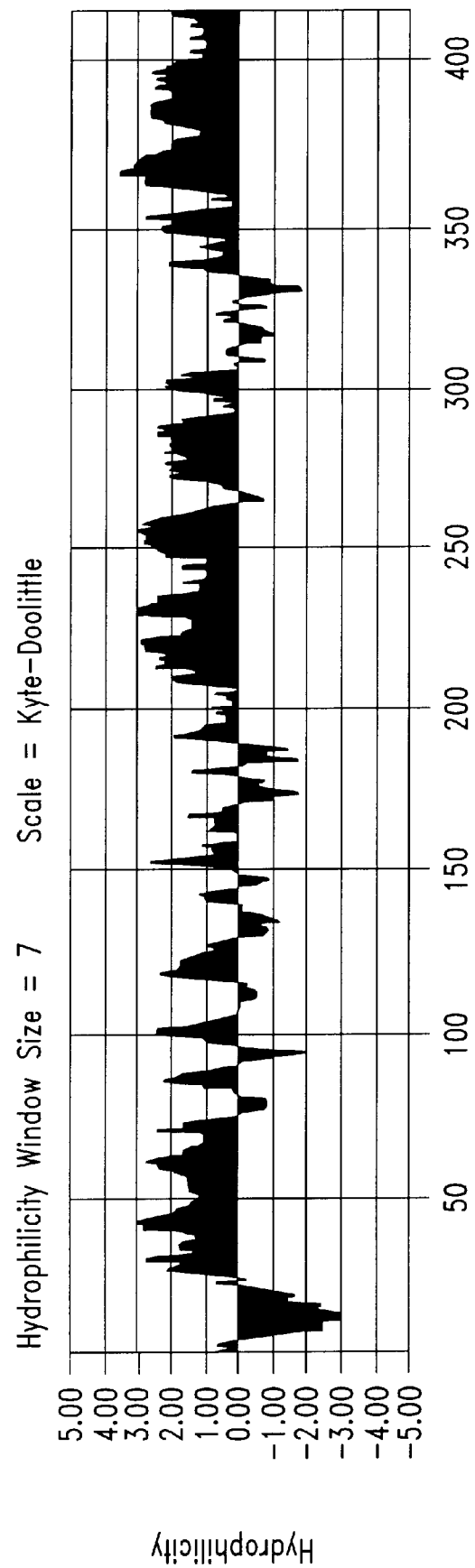
Figure 2A:
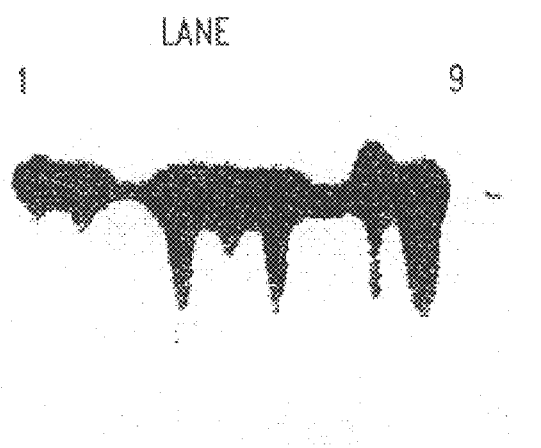
Figure 2B:
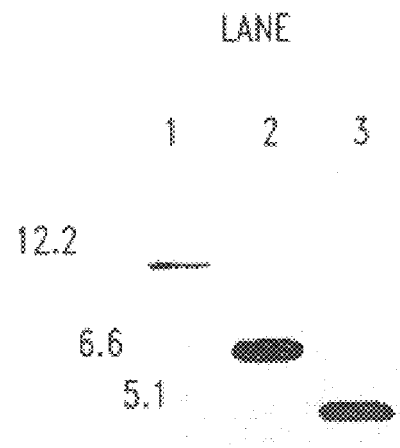

When a castor genomic library (800,000 recombinants) is screened with the calreticulin cDNA, two clones of 6 and 8 kb belonging to only one class of genomic DNA are isolated. Both of these genomic clones hybridized to subclones containing the 5' and 3' ends of the cDNA. The smaller 6 kb genomic fragment is subcloned, and the genomic structure is determined. The full sequence of the castor calreticulin gene is shown in SEQ ID NO:3. The transcribed portion of the calreticulin gene begins at base 60. It corresponds to the 1.5 kb mRNA sequence and is contained in about 3 kb of chromosomal DNA, in agreement with the Southern blot analysis of (FIG. 2B). There are 13 exons and 12 introns contained in this gene, the lengths of which are shown in the following table.

| Exon No. | Exon Coordinates | | Size | Intron No. | Intron Co-ordinates | | Size |
|---|---|---|---|---|---|---|---|
| 1 | 84 | 171 | 89 | 1 | 172 | 771 | 600 |
| 2 | 772 | 879 | 108 | 2 | 880 | 980 | 101 |
| 3 | 981 | 1173 | 193 | 3 | 1174 | 1264 | 91 |
| 4 | 1265 | 15232 | 59 | 4 | 1524 | 1607 | 84 |
| 5 | 1608 | 1664 | 57 | 5 | 1665 | 1768 | 104 |
| 6 | 1769 | 1816 | 48 | 6 | 1817 | 1905 | 89 |
| 7 | 1906 | 1992 | 87 | 7 | 1993 | 2078 | 86 |
| 8 | 2079 | 2204 | 126 | 8 | 2205 | 2282 | 78 |
| 9 | 2283 | 2378 | 96 | 9 | 2379 | 2460 | 82 |
| 10 | 2461 | 2508 | 48 | 10 | 2509 | 2622 | 114 |
| 11 | 2623 | 2652 | 30 | 11 | 2653 | 2729 | 77 |
| 12 | 2730 | 2825 | 96 | 12 | 2826 | 2919 | 94 |
| 13 | 2920 | 2928 | | | | | |

Introns contribute 1.6 kb and exons 1.53 kb to the gene. There is a marked AT bias (63%) in the castor gene base composition, although the AT content of the cDNA is 58%. Twelve of the introns are 120 nt or shorter in length, and are predominantly type O introns (Traut, *Proc. Natl. Acad. Sci. USA* 85:2944–2948, 1988). The intron/exon junction sequences are highly homologous to the vertebrate consensus sequences (Traut, supra).

The introns do not clearly fall between the predicted structural domains of the calreticulin molecule (Smith & Koch, *EMBO J.* 8:3581–3586, 1989). However, intron 1 falls between the signal peptide sequence (Von Heijne, *Biochim. Biophys. Acta* 947:307–333, 1988) and the first ten amino acids of the mature protein, and introns 4–6 interrupt the lysine rich repeats of the central P domain. Intron 12 separates the last 3 amino acids and the termination codon (DEL*) of the mature protein from the preceding exon.

Figure 4A:
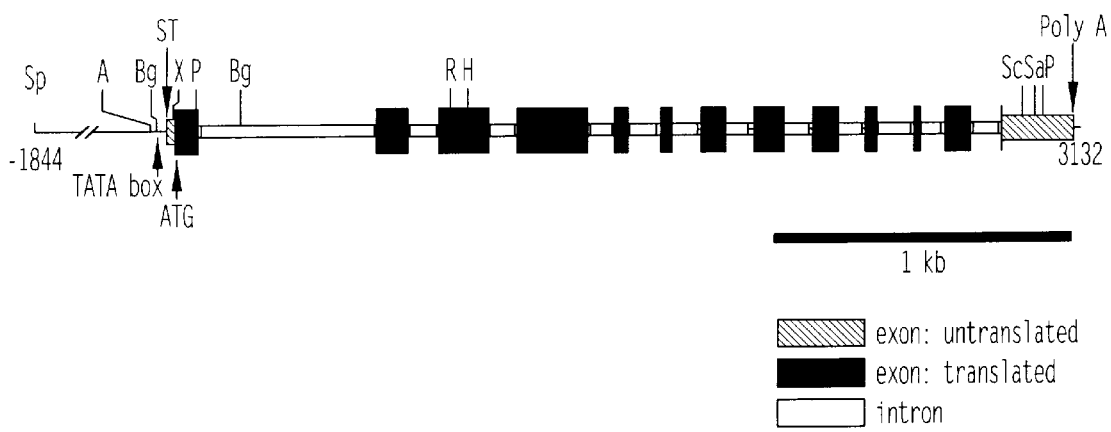
Figure 4B:
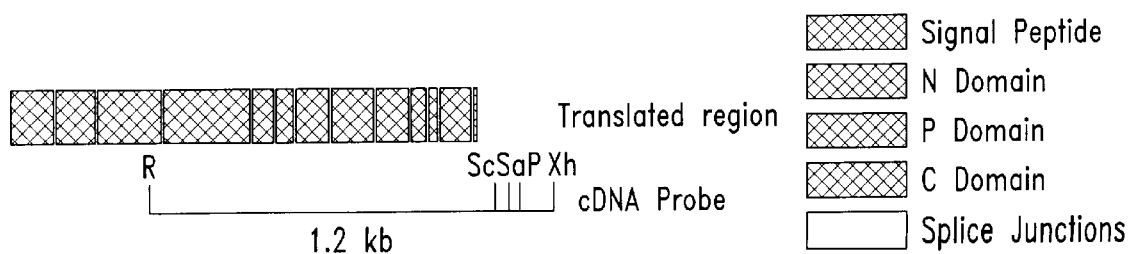
Figure 6:
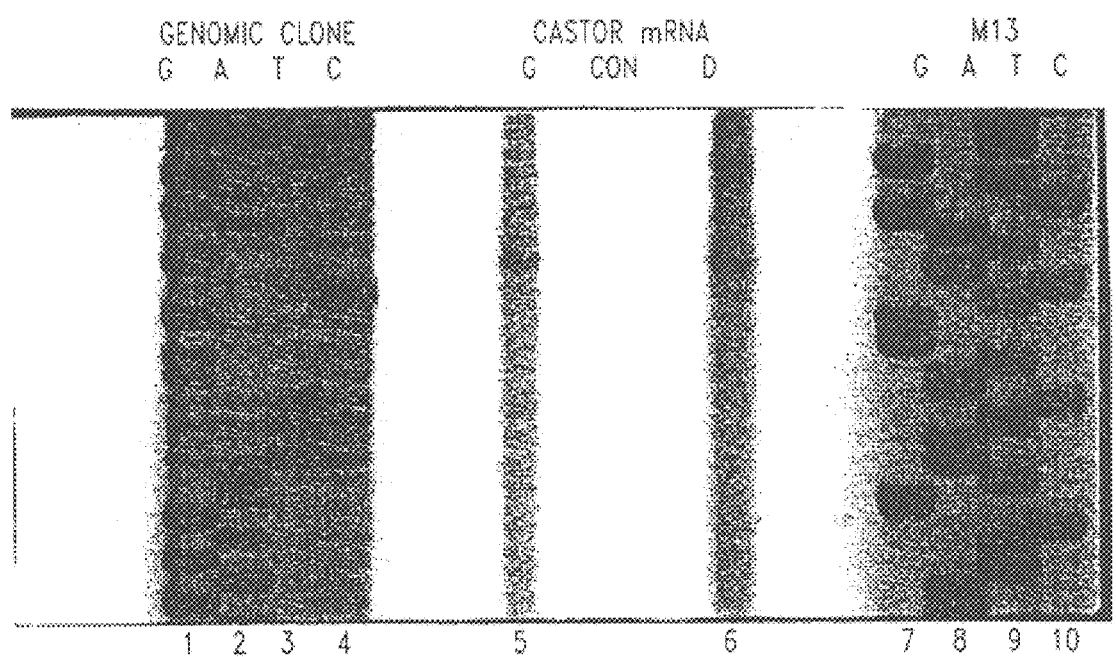

The calreticulin gene contains 12 translated exons (FIGS. 3A, 3B, and 4). The genomic clone contained 1.84 kb of sequence 5' from the translation start site (SEQ ID NO:3). The transcriptional start site is mapped by primer extension (FIG. 6). One start site begins at the A 27 nt upstream from the ATG translational start codon. The 5' UTR of the mature mRNA is thus only 27 nt. This genomic sequence also has a marked AT bias in its base composition (AT content 66.5%). Within the 5' flanking region are several putative regulatory sequences. These include a TATA box (at nt −31 to −27), and several CCAAT box elements (at nt −185, −512, −1019). There is also a GC rich region at nt −1004, a putative SP1 site at nt −1077, a number of putative G box elements clustered at nt −1544 and −1551, at nt −1615 and −1622, and one gbf element at nt −491 (FIG. 5).

Example 2

Cloning of the Gene for *Ricinus communisl* Calnexin

The castor calnexin gene was also isolated as described above. This cDNA (SEQ ID NO:5) is approximately 2 kb and encodes a 542 amino acid protein (SEQ ID NO:6). The genomic sequence is presented in SEQ ID NO:7. Calnexin has 6 exons (FIG. 11). The promoter region is presented in SEQ ID NO:8. Potential promoter elements in the calnexin promoter sequence (SEQ ID NO:8) include an AGC motif (AGCCGCC) at nucleotide −456, an AuxCore (CACCAT) at −407, a CHS/Pal Bx1 site (WCTMACCTAMCM) (SEQ ID NO:9) at −505, a GH2/4 CON site (TCATCTTCTT) (SEQ ID NO:10) at −538, a GH3 $2_{nd}$ site (TGACGTAA) at −706, −434, −288, a GT-1 rbc54 site (ATCATTTCNACT) (SEQ ID NO:11) at −260, a His hexamer site (ACGTCA) at −522 and −382, an HSE Plant site (NTTCNNGAANNTTCNNGAAN) (SEQ ID NO:12) at −139, an MYB-maize site (CCWACC) at −666, a NOSAux site (GCANCATRCRY) (SEQ ID NO:13) at −408 and −417, an 02 box (GATGAYRTGR) (SEQ ID NO:14) at −687, −524, −581, −400, and −384, a 7CA motif (TCATCTTCTT) (SEQ ID NO:15) at −538 and a wound related site (AAGCGTAAGT) (SEQ ID NO:16) at −471 and −21.

Example 3

Expression of Recombinant *Ricinus communis* Calreticulin

The cDNA encoding the mature calreticulin (minus the signal peptide) is amplified by PCR (15–20 cycles) from the full-length cDNA in Bluescript SK using Taq polymerase and primers with an engineered in-frame NdeI site (sense), and an in-frame stop codon and BamHI site (antisense).

The resulting fragment is purified by phenol/chloroform extraction and ethanol precipitation (Sambrook et al., supra), digested overnight with NdeI/BamHI, and purified by agarose gel electrophoresis. The band of interest is excised from the gel and purified using a band Prep kit (Pharmacia, Piscataway, N.J.) and ligated into the NdeI/BamHI site of pET-3a (Novagen, Madison, Wis.). The 5' splice site of the plasmid is sequenced to confirm in-frame insertion. The plasmid is then transformed into the *E. coli* host strain BL21DE3plysS (Studier et al., *Methods Enzymol.* 185:60–89, 1990).

This strain is grown on 2× YT medium with 100 µg/ml ampicillin at 37° C. with vigorous aeration (250 rpm) until the absorbance at 600 nm =0.8, when expression is induced by the addition of isopropyl B-D-thiogalactopyranoside (final concentration 1 mM), and grown for an additional 3 h. Cells are pelleted and stored at −80° C. until use.

Recombinant protein is purified to apparent homogeneity by selective ammonium sulfate precipitation, ion exchange and hydroxyapatite chromatography essentially as described (Milner et al., *J. Biol. Chem.* 266:7155–7165, 1991). Protein concentration is determined as in Bradford (*Anal. Biochem.* 72:248–254, 1976).

Example 4

Preparation of Anti-Calreticulin Antibodies Using Recombinant *Ricinus communis* Calreticulin Immunogen comprising 1 mg of purified recombinant calreticulin is dissolved in 0.1% SDS, 150 mM NaCl, 10 mM sodium phosphate pH 7.5, 2 ml final volume. The primary inoculation of 0.2 mg protein emulsified with an equal amount of Freunds complete adjuvant (0.8 ml final volume) is injected intradermally into rabbits at four sites. Secondary inocula of 0.2 mg protein are emulsified in an equal volume of Freund's incomplete adjuvant and injected. Antibodies are screened by immunoblotting proteins after electrophoretic transfer (Matsudaira, *Methods Enzymol.* 182:602–613, 1990). The membranes are blocked with 1% BSA in Tris-buffered saline, and then incubated with antisera as described (Sambrook et al., supra). Antibody binding is detected with alkaline phosphatase conjugated second antibodies and a standard color development reaction according to the recommendations of the manufacturer (Promega, Madison, Wis.).

When antisera raised against the recombinant calreticulin is used to probe an immune blot of purified castor endosperm endoplasmic reticulum subfractions (FIG. 8C), strong antigenic reactivity is seen to a 50 kDa polypeptide. $^{45}Ca$ binding to calreticulin is confirmed (FIG. 8B). PDI is prominently seen as a 55 kDa band. Calreticulin protein is predominantly found in the Triton X-100 supernatant subfraction, which contains the reticuloplasmins and peripheral ER membrane proteins (FIG. 8A, lane 1 arrow) confirming the ER lumenal location of calreticulin in plants. This antisera cross-reacted to some extent with the ER resident membrane protein calnexin, which has been shown to have significant sequence homology to calreticulin in the central globular domain (Bergeron et al., *Trends Biochem. Sci.* 19:124–128, 1994).

Example 5

Calcium Binding By Recombinant Calreticulin

Calcium binding capacity of the purified recombinant calreticulin is determined by dot blot analysis under non-equilibrium conditions as described (Macer & Koch, *J. Cell Sci.* 91:61–70, 1988). Aliquots of protein (1–10 µg) are spotted onto nitrocellulose membrane (0.45 µm. Schleicher & Shuell, Keene, N.H.) and air dried. The dot blots are incubated in 10 mM Tris-Cl pH 7.5, 100 mM KCl, 0–10 mM $CaCl_2$, 2 µCi/ml ($^{45}Ca)Cl_2$, in a final volume of 10 ml for 10–20 min. at 25° C. with rotation. After brief washing in incubation medium (minus $^{45}CaCl_2$), radioactivity of the dot blots is determined in a liquid scintillation counter (Packard Tri Carb 2700TR).

Figure 7A:
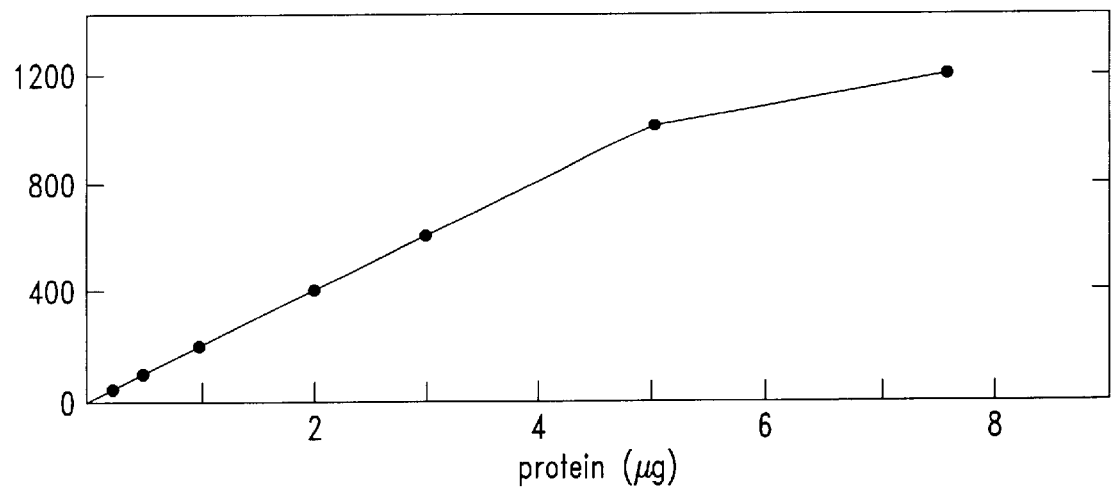
Figure 7B:
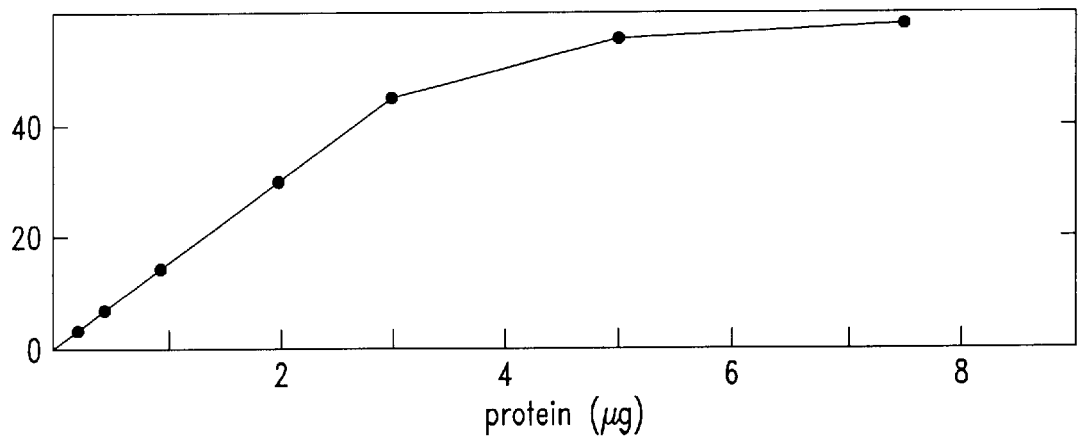
Figure 7C:
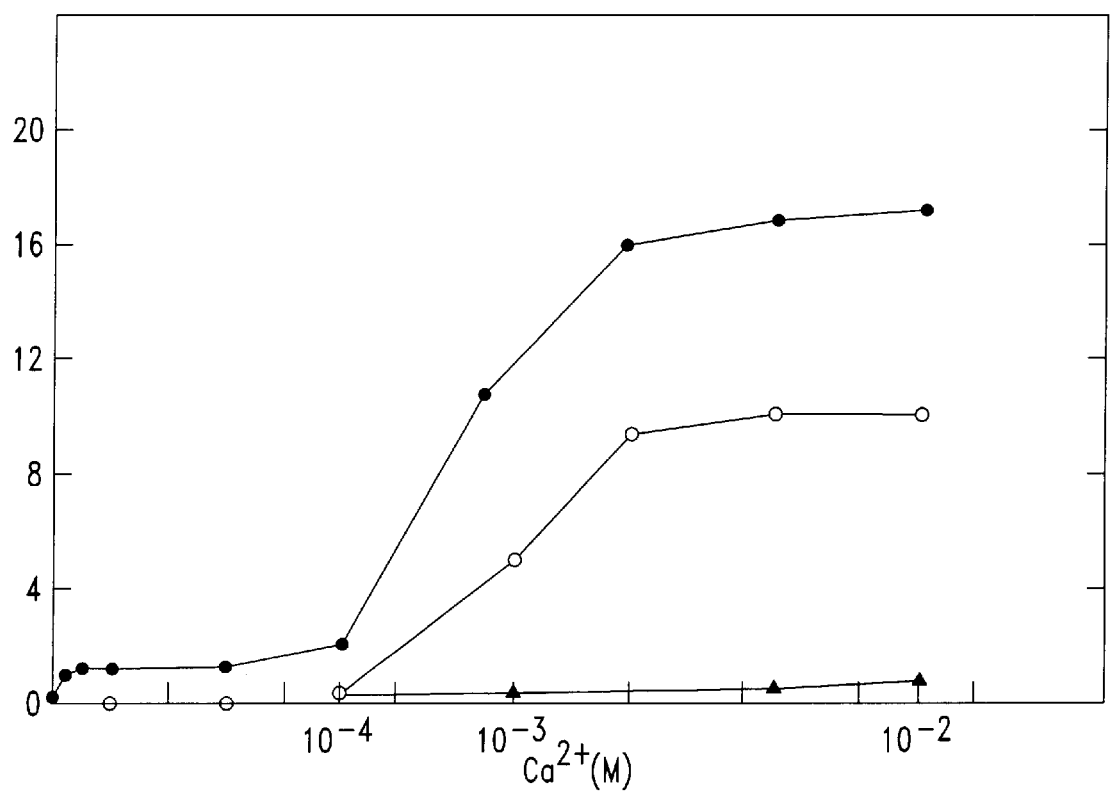

The recombinant protein appeared to have identical calcium binding properties to those described for both the native and recombinant higher eukaryotic calreticulin (Baksh & Michalak, *J. Biol. Chem.* 266:21458–21465, 1991). Calcium binding studies (FIG. 7) of the recombinant protein showed two calcium binding sites, a high affinity (~10 µm $Ca^{2+}$ low capacity (1 mol $Ca^{2+}$+/mol calreticulin) site and a high capacity (10–15 moles $Ca^{2+}$/mole calreticulin) low affinity (0.5 mM $Ca^{2+}$) site. This binding is abolished by the presence of the calcium chelator EGTA. Additionally, 1 mM $MgCl_2$ had no effect on the binding of calcium to the high affinity site, but reduced binding of calcium to the low affinity site by about 50%. The presence of both of these sites in the recombinant protein demonstrates that the recombinant calreticulin correctly folds in *E. coli*. In contrast, recombinant castor PDI (Coughlan et al., *Eur. J. Biochem.* 275:215–224, 1996) also bound calcium, but only with low affinity (~0.6 mM) and high capacity (~12 mole $Ca^{2+}$/mole PDI, FIG. 7, panel B).

Example 6

Recombinant Calreticulin Specifically Binds To Reticular Protein Disulfide Isomerase (PDI)

Calreticulin, in addition to its calcium binding properties, also functions as a molecular chaperone. In this example, a specific calcium-dependent association between calreticulin and PDI is demonstrated for a plant system.

Purified recombinant calreticulin is radioactively labeled using $^{125}I$- Bolton Hunter reagent (Langone, *Methods in Enzymol.* 70:21–247, 1989) obtained from Amersham (Arlington Hts., Ill.). Identification of polypeptides specifically associating with $^{125}I$-calreticulin is carried out by gel overlays as in Bums & Michalak (*FEBS Letts,* 318:181–185, 1993).

When protein blots of castor ER subfractions are overlaid with $^{125}I$ calreticulin, a doublet is observed at ~50–55 kDa (FIG. 9A, lane 1) in the reticuloplasmin enriched (Triton X-100 soluble) fraction, but not in the ER membrane (Triton X100 pellet, FIG. 9A, lane 2). The binding of calreticulin to these proteins appears to be specific, as dilution of the label with unlabelled recombinant calreticulin abolished labeling (FIG. 9A, lane 3), and there is no evidence of calreticulin self associating. The binding appears to be somewhat sensitive to calcium, as the presence of 5 mM calcium inhibited binding (data not shown). The 55 kDa band is identical in electrophoretic mobility to that of PDI, the most abundant reticuloplasmin of this class of ER (Coughlan et al., *Eur. J. Biochem.* 275:215–224, 1996). A specific association between calreticulin and PDI is confirmed by passing detergent solubilized ER through a calreticulin affinity column. Only the 55 kDa protein specifically bound in the presence of EGTA, and this protein is eluted at high salt (FIG. 9B). Furthermore, this protein is confirmed to be PDI by immunoblot analysis. (FIG. 9B).

Example 7

Tissue-Specific Regulation of Plant Gene Expression By the *Ricinus communis* Calreticulin Promoter Genomic DNA sequences mapping 5' to the coding regions of calreticulin are placed upstream of the *E. coli* β-glucuronidase gene (from the uidA locus) in the plasmid pBI121 (Jefferson et al., *EMBO J.* 6:3901–3907, 1987). pBI121 is a BIN 19 derivative that contains the CaMV35S promoter 5' to the β-glucuronidase coding region and a plant selectable marker (kan') between the tDNA sequences required for transfer of DNA into plant cells via *Agrobacterium tumefaciens.* The CaMV 35S promoter is removed with a partial SphI and complete XbaI digest. A 1.8 kb SphI XbaI fragment containing the 5' flanking region six nucleotides from the start of translation of the castor calreticulin gene is ligated to the "promoterless" pBI121 to create calpro/pBI121. This construct is used to transform tobacco leaf discs via *Agrobacterium tumefaciens* mediated transformation. Histochemical analysis of tissue sections is performed by adding 100 mg of the substrate, 5-bromo-4-chloro-3-indoyl-glucuronide sodium salt (pBiosynth AG) in 2 ml of DMSO (Sigma, St. Louis, Mo.) to 200 ml of 10 mM EDTA, 0.1% (v/v) Triton X-100, 0.1 M sodium phosphate pH 7.0, and 0.5 mM potassium ferrocyanide. Plant tissue is incubated in the above mixture at 37° C. overnight and β-glucuronidase activity is determined calorimetrically (Jefferson, *Plant Molecular Biology Reporter* 5:387–405, 1987).

When various tissues of transgenic tobacco containing the chimeric calreticulin-GUS gene are examined, strong enzymatic activity is observed in the floral regions of the plant, as well as in the developing and germinating seed (FIG. 10). In contrast, GUS staining of the vegetative tissue is not as strong, particularly in the leaves. The primary staining region of this tissue is the vasculature, especially the root tip (FIG. 10). In contrast to the Northern blot data (FIG. 2A), the pattern of GUS staining suggests a more localized pattern of distribution of calreticulin, which is predominantly associated with organs of the plant actively involved in export of proteins via the secretory system.

Tissues of transgenic tobacco containing the chimeric calreticulin-GUS gene exhibit strong GUS activity in the floral regions of the plant including developing and germinating seeds and the vasculature. Photosynthetic tissues, especially mature leaves, lack measurable GUS activity. This pattern of expression is consistent with reports showing low steady state levels of RNAs encoding calreticulin and other chaperone proteins in normal barley and tobacco leaves (Chen et al., *Plant Cell* 6:835–843, 1994; Denecke et al., *The Plant Cell* 7:391–406, 1995). Recently, Menegazzi et al., (*Biochem. Biophys. Res. Commun.* 190:1130–1135, 1992) and Navazio et al., (*Plant Physiol.* 109:983–990, 1995) show that small amounts of calreticulin are present in photosynthetic tissue and may be associated with the vasculature. Such vascular localization has been demonstrated for PDI by immune gold labeling and light microscopy (Shorrosh et al., *Plant Physiol.* 103:719–726, 1993). Interestingly, induction of the pathogenesis response in leaves leads to deregulation of ER chaperone proteins, as the PR proteins are all secreted (Denecke et al., *Plant Cell* 7:391–406, 1995). Therefore, the calreticulin promoter is presumed to contain wound responsive elements.

We claim:

1. An isolated nucleic acid molecule encoding calreticulin, comprising a nucleic acid sequence that encodes SEQ ID NO:2, or a conservatively substituted variant thereof wherein the variant has chaperone and calcium binding activity.

2. The isolated nucleic acid molecule according to claim 1 wherein said nucleic acid sequence is SEQ ID NO:1.

3. A vector, comprising the nucleic acid molecule encoding calreticulin according to claim 2.

4. The vector according to claim 3 wherein said vector is an expression vector.

5. A vector, comprising the nucleic acid molecule encoding calreticulin according to claim 1.

6. The vector according to claim 5 wherein said vector is an expression vector.

7. The vector of claim 6 wherein the vector is a binary *Agrobacterium tumefaciens* plasmid vector.

8. An isolated nucleic acid molecule, comprising the nucleic acid sequence of SEQ ID NO:4, or a fragment thereof which has calreticulin-promoter activity.

9. A vector, comprising a nucleic acid molecule containing a calreticulin promoter according to claim 8.

10. The vector according to claim 9, further comprising a nucleic sequence encoding a foreign gene operably linked to said promoter.

11. The vector according to claim 10 wherein said foreign gene confers resistance to a disease caused by a pathogen selected from the group consisting of Sclerotinia, sunflower head moth, canola flea beetle and soybean cyst nematode.

12. The vector according to claim 9, further comprising a selectable marker.

13. A host cell containing a vector according to any one of claims 3, 4, 5, 6, 7, 9, 10, 11 or 12.

14. The host cell of claim 13 wherein the host cell is a plant cell.

15. The host cell of claim 14 wherein said plant cell is selected from the group consisting of soybean, canola, sunflower and alfalfa.

16. A method of producing a foreign gene product, comprising:
   (a) introducing a vector according to claim 9 into a host cell, wherein the vector contains a foreign gene in an expressible form; and
   (b) growing the host cell under conditions wherein the foreign gene is expressed.

17. The method of claim 16 wherein said host cell is a plant cell.

18. The method of claim 17 wherein said plant cell is selected from the group consisting of soybean, canola, sunflower and alfalfa.

19. The method of claim 17 wherein the vector is introduced by transfection by Agrobacterium co-cultivation or bombardment.

* * * * *

UNITED STATES PATENT AND TRADEMARK OFFICE
CERTIFICATE OF CORRECTION

PATENT NO. : 6,171,864 B1
DATED : January 9, 2001
INVENTOR(S) : Sean J. Coughlan and Ron J. Winfrey, Jr.

It is certified that error appears in the above-identified patent and that said Letters Patent is hereby corrected as shown below:

Column 46, claim 19,
Lines 63 through 65, "The method of claim 17 wherein the vector is introduced by transfection by Agrobacterium co-cultivation or bombardment." should read
-- The method of claim 17 wherein transfection is by Agrobacterum co-cultivation or bombardment. --

Signed and Sealed this

Twentieth Day of November, 2001

Attest:

*Nicholas P. Godici*

NICHOLAS P. GODICI
*Attesting Officer*     *Acting Director of the United States Patent and Trademark Office*